United States Patent
Tahara

(10) Patent No.: US 11,000,221 B2
(45) Date of Patent: May 11, 2021

(54) PROGRAM AND SYSTEM FOR EARLY DETECTION AND PREVENTION OF MILD DEMENTIA

(71) Applicant: SHIKUUKANKOUBOU CO.,LTD., Tokyo (JP)

(72) Inventor: Hirofumi Tahara, Tokyo (JP)

(73) Assignee: SHIKUUKANKOUBOU CO., LTD., Tokyo (JP)

( * ) Notice: Subject to any disclaimer, the term of this patent is extended or adjusted under 35 U.S.C. 154(b) by 0 days.

(21) Appl. No.: 15/829,983

(22) Filed: Dec. 4, 2017

(65) Prior Publication Data
US 2018/0125409 A1 May 10, 2018

Related U.S. Application Data

(63) Continuation of application No. PCT/JP2016/066615, filed on Jun. 3, 2016.

(30) Foreign Application Priority Data

Jun. 5, 2015 (JP) .............................. JP2015-115074

(51) Int. Cl.
*A61B 5/00* (2006.01)
*A61B 10/00* (2006.01)
(Continued)

(52) U.S. Cl.
CPC ........ *A61B 5/4088* (2013.01); *A61B 5/04842* (2013.01); *A61B 5/162* (2013.01);
(Continued)

(58) Field of Classification Search
CPC ......... A61B 5/11; A61B 5/4094; A61B 5/163; A61B 3/18; G06F 3/013
(Continued)

(56) References Cited

U.S. PATENT DOCUMENTS 7,567,693 B2* 7/2009 deCharms .............. A61B 5/055
378/4
2002/0091321 A1* 7/2002 Goldstein ............ A61B 5/0059
600/476
(Continued)

FOREIGN PATENT DOCUMENTS

JP 2010-259634 A 11/2010
JP 2012-088776 A 5/2012
(Continued)

OTHER PUBLICATIONS

International Search Report for PCT/JP2016/066615 dated Jul. 12, 2016.
PCT written opinion dated Jul. 12, 2016.

*Primary Examiner* — May A Abouelela
(74) *Attorney, Agent, or Firm* — Yokoi & Co., U.S.A.; Toshiyuki Yokoi

(57) ABSTRACT

To achieve early detection and prevention of mild dementia by viewing with both left and right eyes in a balanced manner based on the balanced stimulation and activation of the left and right brains to easily mitigate the progression of cognitive function decline and promoting recovery of cerebral vision.
The invention consists of: generating a stereoscopic image area A2 for displaying stereoscopic images; displaying a plurality of objects Ob21, Ob22 within a virtual space constructed in the stereoscopic image area A2 with the positions or orientations thereof changing, rotating the plurality of objects Ob21, Ob22 at an arbitrary speed centered on an arbitrary centroid position P2 established within the virtual space, and also changing the color of the objects at an arbitrary timing and duration; and recording as a test result of spatial recognition ability and situational judgment ability the time difference between the timing and duration of the change in color of the objects Ob21, Ob22 and a user
(Continued)

operation on user interfaces G22, G23 as well as the accuracy of the user operation.

2 Claims, 16 Drawing Sheets

(51) Int. Cl.
*A61B 5/16* (2006.01)
*H04N 13/10* (2018.01)
*H04N 13/20* (2018.01)
*A61B 5/0484* (2006.01)
*G09B 19/00* (2006.01)
*H04N 13/128* (2018.01)
*H04N 13/139* (2018.01)
*H04N 13/31* (2018.01)
*H04N 13/359* (2018.01)
*A61B 5/04* (2006.01)

(52) U.S. Cl.
CPC ............. *A61B 10/00* (2013.01); *H04N 13/10* (2018.05); *H04N 13/20* (2018.05); *A61B 5/04012* (2013.01); *A61B 5/7246* (2013.01); *A61B 5/7475* (2013.01); *G09B 19/00* (2013.01); *H04N 13/128* (2018.05); *H04N 13/139* (2018.05); *H04N 13/31* (2018.05); *H04N 13/359* (2018.05)

(58) Field of Classification Search
USPC ............. 600/558, 476, 410, 300; 348/211.2; 434/236
See application file for complete search history.

(56) References Cited

U.S. PATENT DOCUMENTS

| | | | | |
|---|---|---|---|---|
| 2002/0099305 A1* | 7/2002 | Fukushima | ............ | A61B 3/112 600/558 |
| 2002/0103429 A1* | 8/2002 | deCharms | ............ | A61B 5/055 600/410 |
| 2004/0092809 A1* | 5/2004 | DeCharms | ......... | G01R 33/4806 600/410 |
| 2004/0165076 A1* | 8/2004 | Nishimura | ............ | G06T 1/0007 348/211.2 |
| 2005/0186591 A1* | 8/2005 | Bumcrot | ............ | C12N 15/113 435/6.16 |
| 2005/0228785 A1* | 10/2005 | Wolcott | ............ | G06F 19/00 |
| 2005/0283053 A1* | 12/2005 | deCharms | ............ | A61B 5/055 600/300 |
| 2007/0105803 A1* | 5/2007 | Manoharan | ............ | C12N 15/111 514/44 A |
| 2007/0123757 A1* | 5/2007 | Chervinsky | ............ | G16H 10/20 600/300 |
| 2007/0218439 A1* | 9/2007 | Delahunt | ............ | G09B 7/02 434/236 |
| 2011/0218456 A1 | 9/2011 | Graham et al. | | |
| 2012/0094754 A1 | 4/2012 | Suzuki et al. | | |
| 2013/0208245 A1* | 8/2013 | Campbell | ............ | A61B 3/0025 351/246 |
| 2013/0252215 A1 | 9/2013 | Wu et al. | | |
| 2014/0024971 A1* | 1/2014 | Bunn | ............ | A61B 5/11 600/595 |
| 2014/0085446 A1* | 3/2014 | Hicks | ............ | G09B 21/008 348/62 |
| 2014/0243686 A1* | 8/2014 | Kimmel | ............ | A61B 5/1114 600/476 |
| 2014/0278455 A1* | 9/2014 | Chandrasekaran | ............ | G06Q 30/0203 705/2 |
| 2014/0299775 A1* | 10/2014 | Kimmel | ............ | G06K 9/00771 250/341.8 |
| 2014/0347444 A1* | 11/2014 | Naske | ............ | H04N 13/271 348/46 |
| 2015/0077323 A1* | 3/2015 | Ramaswamy | ............ | G06F 3/012 345/156 |
| 2015/0084949 A1* | 3/2015 | Venkatesh | ............ | H04N 13/275 345/419 |
| 2015/0163478 A1* | 6/2015 | Geiss | ............ | H04N 13/243 348/47 |
| 2015/0294588 A1* | 10/2015 | Kullok | ............ | G09B 5/02 434/236 |
| 2015/0320350 A1 | 11/2015 | Ishikawa et al. | | |
| 2016/0038463 A1* | 2/2016 | Gallagher | ............ | A61P 25/28 514/424 |

FOREIGN PATENT DOCUMENTS

| | | |
|---|---|---|
| JP | 2012-88776 A | 5/2012 |
| JP | 2012-105795 A | 6/2012 |
| JP | 2014-008329 A | 1/2014 |
| WO | 2012/077313 A | 6/2012 |
| WO | 2014/034856 A | 3/2014 |
| WO | 2014/064719 A | 5/2014 |

* cited by examiner

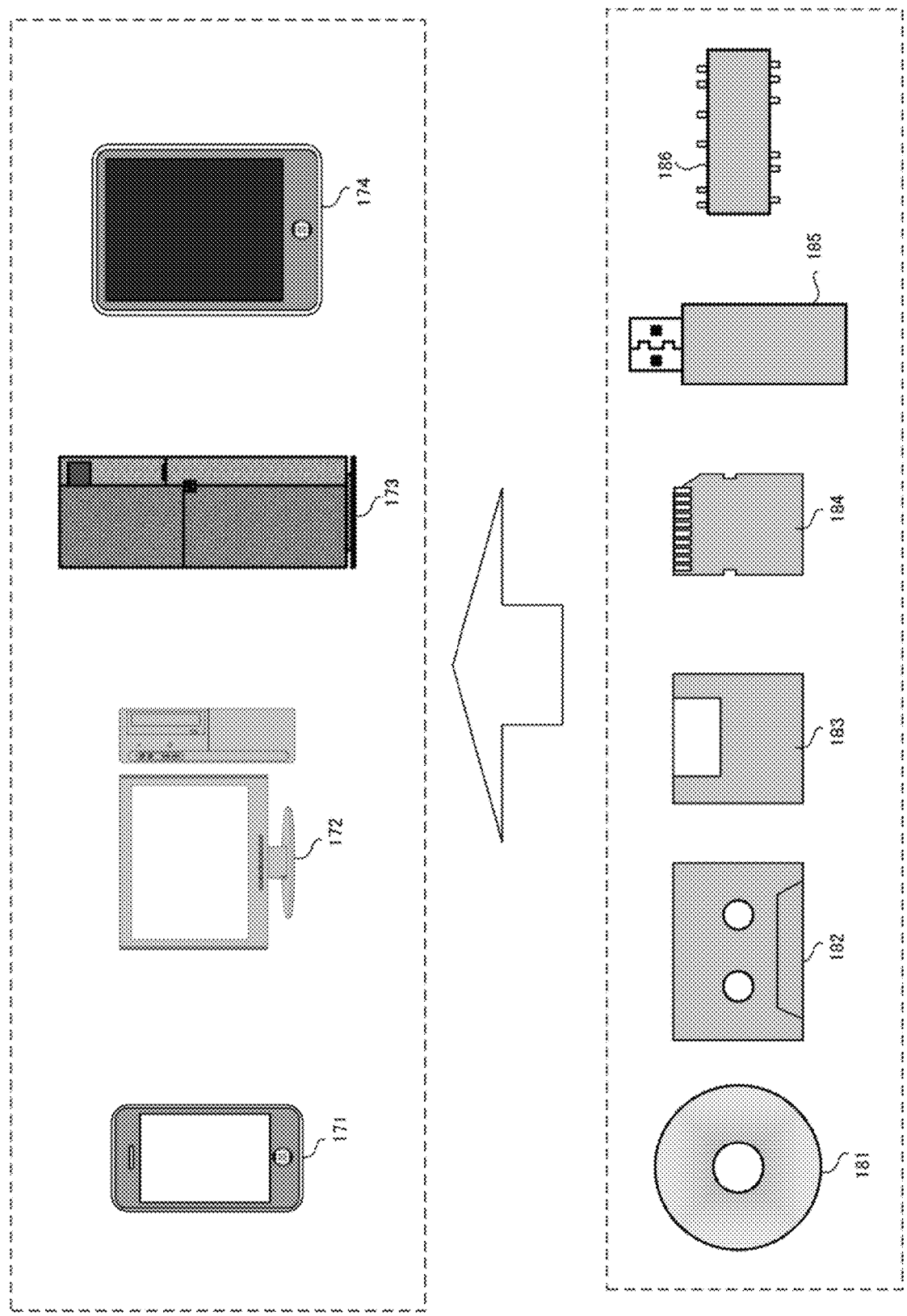

PROGRAM AND SYSTEM FOR EARLY DETECTION AND PREVENTION OF MILD DEMENTIA

CROSS-REFERENCES TO RELATED APPLICATIONS

This Application claims the benefit of priority and is a Continuation application of the prior International Patent Application No. PCT/JP2016/066615, with an international filing date of Jun. 3, 2016, which designated the United States, and is related to the Japanese Patent Application No. 2015-115074, filed Jun. 5, 2015, the entire disclosures of all applications are expressly incorporated by reference in their entirety herein.

BACKGROUND OF THE INVENTION

1. Field of the Invention

The present invention relates to a program and system for early detection and prevention of mild dementia.

2. Description of Related Art

The gray zone between the health condition of slightly concerning impaired cognitive function that cannot be called "Dementia" and dementia is called "Mild Cognitive Impairment (MCI)", research on dementia has progressed and the concept of early detection and treatment, and prevention of mild dementia is being supported.

Dementia with Lewy Bodies (DLB) along with Alzheimer Disease (AD) and vascular dementia are considered to be the 3 main types of dementia, and memory impairment is not significant at an early stage, but impairment of visuospatial ability (constitutional impairment, and visual cognitive impairment) tend to appear from an early stage (refer to Non-Patent Document 1).

On the other hand, the association between reduced visual acuity and cognitive function decline has been drawing attention, and a paper examining the relationship between the decline in visual acuity and decline in cognitive function of the elderly concerning reduced visual acuity with normal cognitive function leads to an increase in risk of dementia such as Alzheimer's disease in the future has been published in the American Journal of Epidemiology (refer to Non-Patent Document 2).

According to this research paper, in a follow-up study of 625 elderly US study participants for around 10 years, the results indicated that the risk of developing dementia was 63% lower for the group who responded visual acuity is "Extremely good" and "Very good" compared with the groups who gave other responses. In addition, the risk for the group who had visited an ophthalmologist was 64% lower compared to the group who had not visited an ophthalmologist, and risk for the group receiving eye treatment was 56% lower than the group that did not receive eye treatment. Compared to the "Group with visual acuity corresponding to 'Extremely good' and 'Very good' and visited an ophthalmologist", the risk of developing Alzheimer's disease was 9.46 times higher for the "Group with poorer visual acuity and did not visit an ophthalmologist", and risk of cognitive function decline that did not lead to dementia also increased 5.05 times.

In other words, although vision impairment was known to possibly appear as an early symptom of Alzheimer's disease, the above study indicates that reduced visual acuity is associated with an increased risk of developing dementia such as Alzheimer's disease in the future when cognitive function is normal, reduction of vision is considered to decrease stimulation to the brain, exercise, and social activity, which may lead to an increased risk of dementia.

On the other hand, for example, the game disclosed in Patent Document 1 is available as the technology to visually activate the brain. In the game disclosed in Patent Document 1, a combination of proper enemy objects and false recognition objects have been mixed to confuse the user, and since the user is required to accurately grasp the facial image of the enemy object, the game requires the user to have processing power and concentration to distinguish enemy objects, and this enables brain activation associated with facial image recognition.

PRECEDING TECHNICAL DOCUMENTS

Non-Patent Documents

[Non-Patent Document 1] Ono Pharmaceutical Co., Ltd. issued "Spring Mind" 2012 No. 11, page 2 to 3

[Non-Patent Document 2] "Untreated Poor Vision: A Contributing Factor to Late-Life Dementia", Mary A. M. Rogers* and Kenneth M. Langa, American Journal of Epidemiology Advance Access published Feb. 11, 2010

Patent Documents

[Patent Document 1] Japanese Unexamined Patent Application Publication No. 2012-088776

BRIEF SUMMARY OF THE INVENTION

Incidentally, ocular acuity and cerebral vision are 2 types of visual acuity, visual acuity due to cognitive function decline is caused by "Reduced cerebral vision" as well as "Reduced brain activity" that is caused due to decline in ocular acuity. Visual acuity due to cognitive function decline is considered to progress with a relation between the eyes and brain.

For this reason, applying stimulus that balances "Viewing" with both the left and right eyes is important in the approach to activate the brain. In other words, well-balanced stimulation of the left and right brains through the cerebral vision of both eyes enhances memory, concentration, and imagination, alleviates the progression of cognitive function decline, and stimulates recovery of cerebral vision.

However, the method disclosed in Patent Document 1 is a simple technique to distinguish objects, since the element for viewing with a good balance using both right and left eyes is not included, this will result in viewing with only the "Dominant eye" because of too much concentration on the game, and there is a possibility that the brain will be stimulated with a biased cerebral vision.

Accordingly, the present invention has been made in view of the above points and the task is to offer a program and system for early detection and prevention of mild dementia that easily mitigates the progression of cognitive function decline and promotes recovery of cerebral vision by viewing with both left and right eyes in a balanced manner based on the balanced stimulation and activation of the left and right brains.

Means for Solving Problem (1) Program Invention (1-1) Spatial Recognition Ability and Situational Judgment Ability Test To resolve the above problem, the present invention is characterized by a program that uses an information processing terminal equipped with, an application execution unit to execute a program for generating a left eye image and right eye image corresponding to the left and right eyes of the observer respectively, and a display unit for displaying the left eye image and right eye image generated by the program executed with the application execution unit at the respective positions corresponding to the left and right eyes, and a user interface that accepts user operations;

for the early detection or prevention of mild dementia, this program performs processing of, a stereoscopic image generating step wherein a stereoscopic image area is generated in which a stereoscopic image constituted by generating a convergence angle and parallax between the left eye image and right eye image is displayed, and An object movement step wherein a plurality of objects is displayed within a virtual space constructed in the stereoscopic image area with the positions or orientations thereof changing, rotating the plurality of objects at an arbitrary speed centered on an arbitrary centroid position established within the virtual space, and also changing the color of the objects at an arbitrary timing and duration, and a cognitive ability measurement step wherein the time difference between the timing and duration of the change in color of the object and user operation on the user interface, and accuracy of the user operation are recorded as the test results for spatial recognition ability and situation judgment ability, on the information processing terminal.

According to the present invention, for example, on a device such as a tablet PC that is capable of 3D display, the color of multiple objects that rotate in arbitrary complex orbits are changed at arbitrary timings and duration in the virtual space within the stereoscopic image area, and the observer is made to operate the user interface on recognizing the change. The spatial recognition ability and situation judgment ability is checked by measuring the time required for the observer to perform the operation from when the object color changes, and accuracy of operations. If this time difference or accuracy exceeds (falls below) a predetermined threshold value, there is a possibility of cognitive impairment, and preventive measures can be taken based on this.

In the above-described invention, inclusion of an additional step for changing the rotation radius of the object or the centroid position which is the rotation center and displaying the object in the entire stereoscopic image area in the object movement step, and also measuring the visual field range of the observer based on the relationship between user operations and display position of the object in the cognitive ability measurement step is preferred.

In this case, the object can be displayed up to the 4 corners of the tablet PC screen, and visual field range of the observer can be measured by observing the reaction of the observer and cognitive impairment can be estimated from the width of the visual field.

In the above-described invention, inclusion of an additional opacity measurement step is preferred wherein the color saturation of the object is changed, color identified by the user is checked based on the relationship between color saturation of the object and user operations on the user interface, and opacity is measured.

In this case, for example, by changing and adjusting the color saturation of the object with slider operation such that the observer can easily see the object, color identification by the observer and opacity of the eyeballs is detected.

(1-2) Tachistoscopic Vision and Size Constancy Test

Also, according to another aspect of the present invention characterized by a program that uses an information processing terminal equipped with an application execution unit to execute a program for generating a left eye image and right eye image corresponding to the left and right eyes of the observer respectively, and a display unit for displaying the left eye image and right eye image generated by the program executed with the application execution unit at the respective positions corresponding to the left and right eyes, and a user interface for accepting a user operation, for the early detection or prevention of mild dementia, this program performs processing of, a stereoscopic image generating step wherein a stereoscopic image area is generated in which a stereoscopic image constituted by generating a convergence angle and parallax between the left eye image and right eye image is displayed, and an object depth variation step, wherein multiple objects whose positions or orientations change within the virtual space constructed in the stereoscopic image area are displayed and multiple objects related to the same item among multiple types of objects are simultaneously displayed while varying the depth in the virtual space, and a constancy measurement step that records the displayed number of objects related to the same item and accuracy of user operation on the user interface as the test results of tachistoscopic vision and size constancy test, on the information processing terminal.

According to the present invention, for example, on a device such as a tablet PC that is capable of 3D display, a plurality of fruits types such as apples and oranges are displayed at the same time while changing the depth, and the observer is made to answer by operating the user interface for the displayed number. The identical items in the virtual space are set to the same size and only the depth (depth in the virtual space) during display is changed. By measuring the number of objects displayed and number of objects counted by the observer, tachistoscopic vision and size constancy of the observer can be checked. If the time taken to answer or number of incorrect answers exceeds (falls below) a predetermined threshold value, there is a possibility of cognitive impairment, and preventive measures can be taken based on this.

In the above-described invention, inclusion of an additional query step is preferred to ask a question on the number of identical objects displayed and accept an answer from the observer when a certain time has passed after the constancy measurement step, and a memory skills measurement step to record the number of objects related to the same item that is displayed and accuracy of the user operation on the user interface as test results of the memory skills test.

In this case, memory can also be checked along with tachistoscopic vision and size constancy. If the number of incorrect answers exceeds (falls below) a predetermined threshold value, there is a possibility of cognitive impairment, and preventive measures can be taken based on this.

(1-3) Color Constancy Test

According to another aspect of the present invention characterized by a program that uses an information processing terminal equipped with an application execution unit to execute a program for generating a left eye image and right eye image corresponding to the left and right eyes of the observer respectively, and a display unit for displaying the left eye image and the right eye image generated by the program executed by the application execution unit at positions corresponding to the left and right eyes, and a user interface for accepting a user operation, for the early detection or prevention of mild dementia, and this program executes the processing of a stereoscopic image generating step wherein a stereoscopic image area is generated in which a stereoscopic image constituted by generating a convergence angle and parallax between the left eye image and right eye image is displayed, an object color variation step to display multiple objects whose positions or orientations change within the virtual space constructed in the stereoscopic image area, and to display objects related to the same item among multiple types of objects by changing the brightness, saturation, color or light source position, and a color constancy measuring step to record the display of the objects related to the same item and accuracy of the user operation on the user interface as results of the color constancy test on the information processing terminal.

According to the present invention, for example, on a device such as a tablet PC that is capable of 3D display, objects related to the same item are displayed by changing the brightness, saturation, color or light source position, and the observer is made to answer the color of the same item by operating the user interface. By comparing the object color with the answer of the observer, color constancy of the observer can be checked. If the time taken to answer or number of incorrect answers exceeds (falls below) a predetermined threshold value, there is a possibility of cognitive impairment, and preventive measures can be taken based on this.

(1-4) Brain Activity Status Test for Visual Cortex

According to another aspect of the present invention characterized by a program that uses an information processing terminal equipped with an application execution unit to execute a program for generating a left eye image and right eye image corresponding to the left and right eyes of the observer respectively, a display unit for displaying the left eye image and the right eye image generated by the program executed by the application execution unit at positions corresponding to the left and right eyes, and a user interface for accepting a user operation, for the early detection or prevention of mild dementia, and this program executes the left and right image generation step to display different number of objects for the left eye image and right eye image, and visual rivalry measurement step to record the objects displayed and accuracy of the user operation on the user interface as the test results for the status of brain activity of visual cortex due to visual rivalry on the information processing terminal.

According to the present invention, for example, on a device such as a tablet PC that is capable of 2D and 3D display, brain activity status of the visual cortex due to visual rivalry can be tested by displaying different number of objects for the left eye image and right eye image in the left and right image areas.

(1-5) Electroencephalogram (EEG) Coupling Test

In the above-described invention, the information processing terminal provided with an additional EEG detection device that detects the electroencephalogram of the observer and outputs electroencephalogram signals corresponding to the electroencephalogram, and an EEG signal recording unit that records the electroencephalogram signals acquired from the EEG detection device, and execution of the process that is provided with an additional electroencephalogram correlation analysis step to link and analyze the test results recorded by the stereoscopic viewing program executed in the application execution unit and the electroencephalogram signals recorded by the EEG signal recording unit by the early detection and prevention program is preferred. EEG is a weak periodic current output from the nerve cells in the brain.

In this case, states of tension, relaxation, and concentration of an observer can be measured by analyzing the strength and balance of various electroencephalograms to understand their correlation with the accuracy of user operations, and this enables accuracy of early detection and prevention of mild dementia to be improved.

More specifically, since cognitive functions diminished by MCI (Mild Cognitive Impairment) are "Episodic memory", "Attention division function", "Thinking ability" and "Visuospatial cognitive function", the onset of cognitive impairment can be delayed or prevented by working towards their improvement with simulation of the cognitive functions. In the analysis unit $111f$, along with stimulating the cognitive functions by means of stereoscopic vision using the stereoscopic viewing program, the effect of stimulation can be analyzed on cognitive functions by detecting the electroencephalogram signals.

"Visuospatial cognitive impairment" is a condition in which the ability to recognize faces or objects, finding objects, operating simple tools, or wearing clothes gets impaired, although visual acuity may not be impaired, and these are the common symptoms of Alzheimer-type dementia. In the early stage of typical Alzheimer-type dementia, there are symptoms such as deterioration in the ability to draw a figure, getting lost while driving, not being able to park a car in the garage, in the middle stage, there are symptoms such as difficulty in finding objects, while in the late stage, there are symptoms such as not being able to operate simple tools and wear clothes.

These symptoms are called visuospatial cognitive impairment and the reduction in blood flow in the parieto-occipital lobe is considered as the responsible focus for visuospatial cognitive impairment in neural base Alzheimer-type dementia. Visuospatial cognitive impairment is often detected by copying overlapping pentagons or three-dimensional shapes in the MMSE. Fox or pigeon gesture imitation test is said to be a simple screening test. This is also referred to as a constitutional impairment that is caused due to the impairment of visuospatial cognitive functions such as grasping the visuospatial characteristics of an object in front of the eyes and then copying or moving the object. A close correlation is considered to exist between cognitive impairment and visuospatial cognitive functions, and by stimulating the brain functions with the stereoscopic viewing program and detecting the brain waves, the effect of stimulation on cognitive functions can be analyzed more effectively.

(1-6) Server Control Program

According to another aspect of the present invention is a server control program for controlling the contents management server that can be connected to the above-mentioned information processing terminal through a communication network, The server control program is a program for the early detection and prevention of mild dementia characterized by making the content management server function as the contents distribution unit that acquires the uploaded images through a content storage unit that stores images in association with the information including age of the subject shown in the image, a communication unit that sends and receives data to and from the program being executed by the application execution unit, a content selection unit that retrieves the delivery request containing the age of the observer being tested from the information processing terminal and selects images conforming to the age of the observer included in the delivery request from the content storage unit, and a content delivery unit that delivers the images selected by the content selection unit to the program executed by the application execution unit.

In this case, many users are asked to upload nostalgic photographs along with information containing age that are accumulated in the form of a database, and images matched with the age of a user who is the subject with cognitive impairment are generated as objects and used in various tests based on the above-mentioned program. As a result, long-term memory of the subject can be evoked during the various tests described above, and activation of the brain can be promoted.

(2) Invention of the System (2-1) Spatial Recognition Ability and Situational Judgment Ability Test The present invention characterized by a system for the early detection or prevention of mild dementia that uses an information processing terminal equipped with an application execution unit to execute a program for generating a left eye image and right eye image corresponding to the left and right eyes of the observer respectively; and a display unit for displaying the left eye image and right eye image generated by the program executed by the application execution unit at positions corresponding to the left and right eyes; and a user interface for accepting a user operation, and this program includes a stereoscopic image generating step wherein a stereoscopic image area is generated in which a stereoscopic image constituted by generating a convergence angle and parallax between the left eye image and right eye image is displayed; An object movement step wherein a plurality of objects is displayed within a virtual space constructed in the stereoscopic image area with the positions or orientations thereof changing, rotating the plurality of objects at an arbitrary speed centered on an arbitrary centroid position established within the virtual space, and also changing the color of the objects at an arbitrary timing and duration; and a cognitive ability measurement step wherein the time difference between the timing and duration of the change in color of the object and user operation on the user interface, and accuracy of the user operation are recorded as the test results for spatial recognition ability and situation judgment ability.

According to the present invention, for example, on a device such as a tablet PC that is capable of 3D display, the color of multiple objects that rotate in arbitrary complex orbits are changed at arbitrary timings and duration in the virtual space within the stereoscopic image area, and the observer is made to operate the user interface on recognizing the change. The spatial recognition ability and situation judgment ability is checked by measuring the time required for the observer to perform the operation from when the object color changes, and accuracy of operations. If this time difference or accuracy exceeds (falls below) a predetermined threshold value, there is a possibility of cognitive impairment, and preventive measures can be taken based on this.

In the above-described invention, inclusion of an additional step for changing the rotation radius of the object or the centroid position which is the rotation center and displaying the object in the entire stereoscopic image area in the object movement step, and also measuring the visual field range of the observer based on the relationship between user operations and display position of the object in the cognitive ability measurement step is preferred.

In this case, the object can be displayed up to the 4 corners of the tablet PC screen, and visual field range of the observer can be measured by observing the reaction of the observer and cognitive impairment can be estimated from the width of the visual field.

In the above-described invention, inclusion of an additional opacity measurement step is preferred wherein the program can change the color saturation of the object, check the color identified by the user based on the relationship between color saturation of the object and user operations on the user interface, and measure opacity.

In this case, for example, by changing and adjusting the color saturation of the object with slider operation such that the observer can easily see the object, color identification by the observer and opacity of the eyeballs is detected.

(2-2) Tachistoscopic Vision and Size Constancy Test

According to another aspect of the present invention characterized by a program that uses an information processing terminal equipped with an application execution unit to execute a program for generating a left eye image and right eye image corresponding to the left and right eyes of the observer respectively, and a display unit for displaying the left eye image and the right eye image generated by the program executed by the application execution unit at positions corresponding to the left and right eyes, and a user interface for accepting a user operation, for the early detection or prevention of mild dementia, and this program executes the processing of a stereoscopic image generating step wherein a stereoscopic image area is generated in which a stereoscopic image constituted by generating a convergence angle and parallax between the left eye image and right eye image is displayed, an object depth variation step wherein multiple objects whose positions or orientations change within the virtual space constructed in the stereoscopic image area are displayed and multiple objects related to the same item among multiple types of objects are simultaneously displayed while varying the depth in the virtual space, and a constancy measurement step that records the displayed number of objects related to the same item and accuracy of user operation on the user interface as the test results of tachistoscopic vision and size constancy test on the information processing terminal.

According to the present invention, for example, on a device such as a tablet PC that is capable of 3D display, a plurality of fruits types such as apples and oranges are displayed at the same time while changing the depth, and the observer is made to answer by operating the user interface for the displayed number. The identical items in the virtual space are set to the same size and only the depth (depth in the virtual space) during display is changed. By measuring the number of objects displayed and number of objects counted by the observer, tachistoscopic vision and size constancy of the observer can be checked. If the time taken to answer or number of incorrect answers exceeds (falls below) a predetermined threshold value, there is a possibility of cognitive impairment, and preventive measures can be taken based on this.

In the above-described invention, inclusion of an additional query step in the program is preferred to ask a question on the number of identical objects displayed and accept an answer from the observer when a certain time has passed after the constancy measurement step, and a memory skills measurement step to record the number of objects related to the same item that is displayed and accuracy of the user operation on the user interface as test results of the memory skills test.

In this case, memory can also be checked along with tachistoscopic vision and size constancy. If the number of incorrect answers exceeds (falls below) a predetermined threshold value, there is a possibility of cognitive impairment, and preventive measures can be taken based on this.

(2-3) Color Constancy Test

According to another aspect of the present invention characterized by a system for the early detection or prevention of mild dementia that uses an information processing terminal equipped with an application execution unit to execute a program for generating a left eye image and right eye image corresponding to the left and right eyes of the observer respectively, and a display unit for displaying the left eye image and the right eye image generated by the program executed by the application execution unit at positions corresponding to the left and right eyes, and a user interface for accepting a user operation, and this program includes a stereoscopic image generating step wherein a stereoscopic image area is generated in which a stereoscopic image constituted by generating a convergence angle and parallax between the left eye image and right eye image is displayed, a color variation step to display multiple objects whose positions or orientations change within the virtual space constructed in the stereoscopic image area, and to display objects related to the same item among multiple types of objects by changing the brightness, saturation, color or light source position, and a color constancy measuring step to record the display of the objects related to the same item and accuracy of the user operation on the user interface as test results of the color constancy test.

According to the present invention, for example, on a device such as a tablet PC that is capable of 3D display, objects related to the same item are displayed by changing the brightness, saturation, color or light source position, and the observer is made to answer the color of the same item by operating the user interface. By comparing the object color with the answer of the observer, color constancy of the observer can be checked. If the time taken to answer or number of incorrect answers exceeds (falls below) a predetermined threshold value, there is a possibility of cognitive impairment, and preventive measures can be taken based on this.

(2-4) Brain Activity Status Test for Visual Cortex

According to another aspect of the present invention characterized by a system for the early detection or prevention of mild dementia that uses an information processing terminal equipped with an application execution unit to execute a program for generating a left eye image and right eye image corresponding to the left and right eyes of the observer respectively, a display unit for displaying the left eye image and the right eye image generated by the program executed by the application execution unit at positions corresponding to the left and right eyes, and a user interface for accepting a user operation, this program includes the left and right image generation step to display different number of objects for the left eye image and right eye image, and visual rivalry measurement step to record the objects displayed and accuracy of the user operation on the user interface as the test results for the status of brain activity of visual cortex due to visual rivalry.

According to the present invention, for example, on a device such as a tablet PC that is capable of 2D and 3D display, brain activity status of the visual cortex due to visual rivalry can be tested by displaying different number of objects for the left eye image and right eye image in the left and right image areas.

(2-5) Electroencephalogram (EEG) Coupling Test

In the above-described invention, the information processing terminal provided with an additional EEG detection device that detects the electroencephalogram of the observer and outputs electroencephalogram signals corresponding to the electroencephalogram, and an EEG signal recording unit that records the electroencephalogram signals acquired from the EEG detection device, and execution of the process that is provided with an additional electroencephalogram correlation analysis step to link and analyze the test results recorded by the stereoscopic viewing program executed in the application execution unit and the electroencephalogram signals recorded by the EEG signal recording unit by the early detection and prevention program is preferred. In this case, states of tension, relaxation, and concentration of an observer can be measured by analyzing the strength and balance of various electroencephalograms to calculate their correlation with the accuracy of user operations, and this enables accuracy of early detection and prevention of mild dementia to be improved.

(2-6) Content Management Server

In the above described invention, provision of an additional contents management server that can be connected to a communication network and is equipped with a contents distribution unit that acquires the uploaded images through a content storage unit that stores the images in association with the information including age of the subject shown in the image, a communication unit that sends and receives data to and from the program being executed by the application execution unit, a content selection unit that retrieves the delivery request containing the age of the observer being tested from the information processing terminal and selects images conforming to the age of the observer included in the delivery request from the content storage unit, and a content delivery unit that delivers the images selected by the content selection unit to the program executed by the application execution unit, and a program to generate objects from the images delivered by the contents delivery unit and execute the tests is preferred.

In this case, many users are asked to upload nostalgic photographs along with information containing age that are accumulated in the form of a database, and images matched with the age of a user who is the subject with cognitive impairment are generated as objects and used in various tests based on the above-mentioned program. As a result, long-term memory of the subject can be evoked during the various tests described above, and activation of the brain can be promoted.

Effect of the Invention

As described above, according to the present invention, early detection and prevention of mild dementia can be achieved by viewing with both left and right eyes in a balanced manner based on the balanced stimulation and activation of the left and right brains to easily mitigate the progression of cognitive function decline and promoting recovery of cerebral vision.

BRIEF DESCRIPTION OF THE DRAWINGS

FIG. 19 is the recording media for recording the program according to the embodiment.

DETAILED DESCRIPTION OF THE INVENTION

The embodiment of the program and system for early detection and prevention of mild dementia of the present invention will be explained in detail with reference to the diagrams.

(Overall Configuration of the System)

Figure 1:
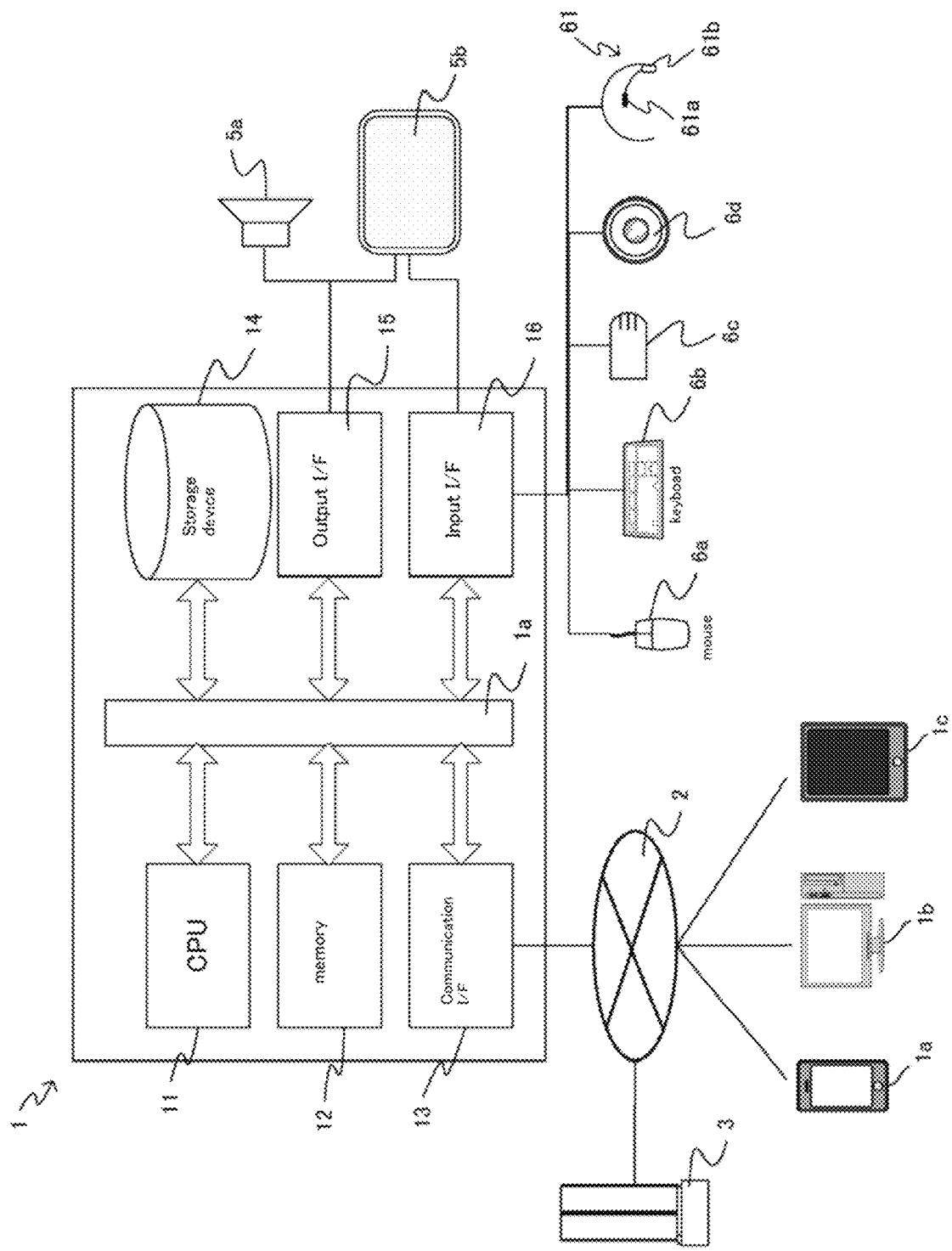
FIG. 1 is a block diagram showing the overall configuration of a system for early detection and prevention of mild dementia according to the embodiment.
Figure 2A:
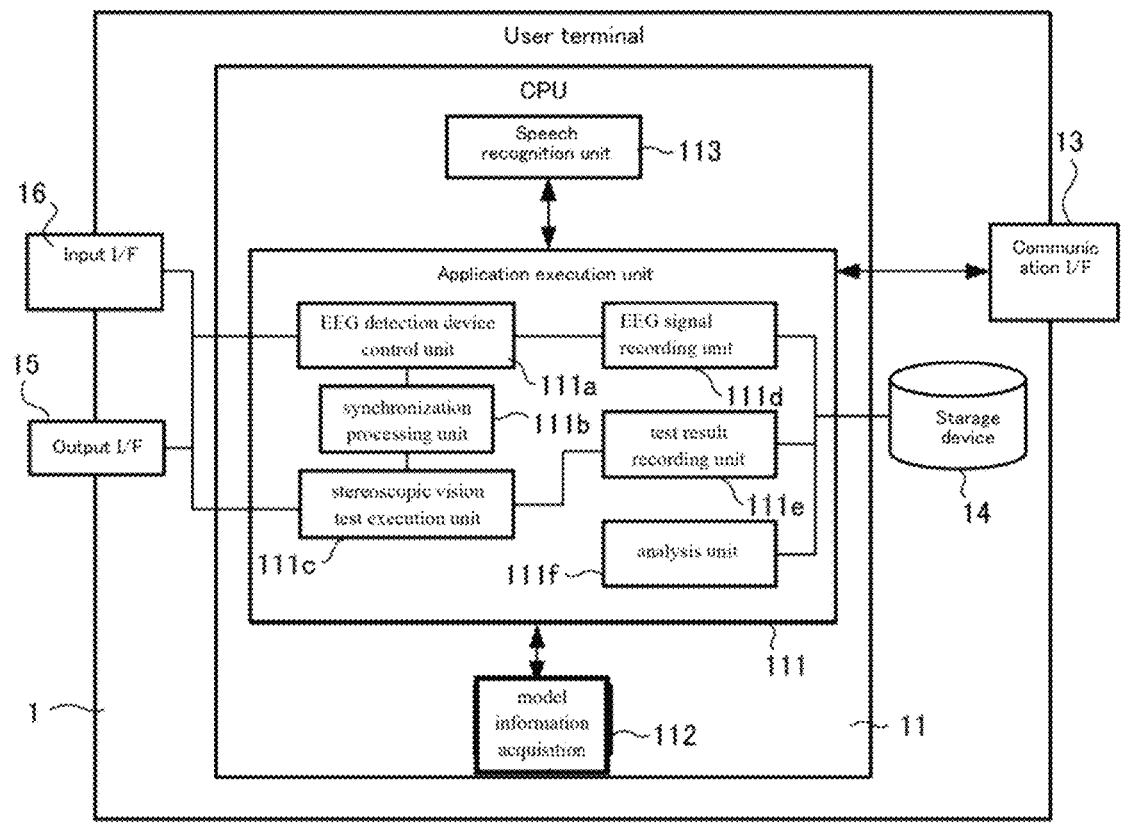
FIG. 2A is a block diagram showing the modules related to a function for early detection and prevention of mild dementia that is virtually constructed on a CPU of an information processing terminal according to the present embodiment.
Figure 2B:
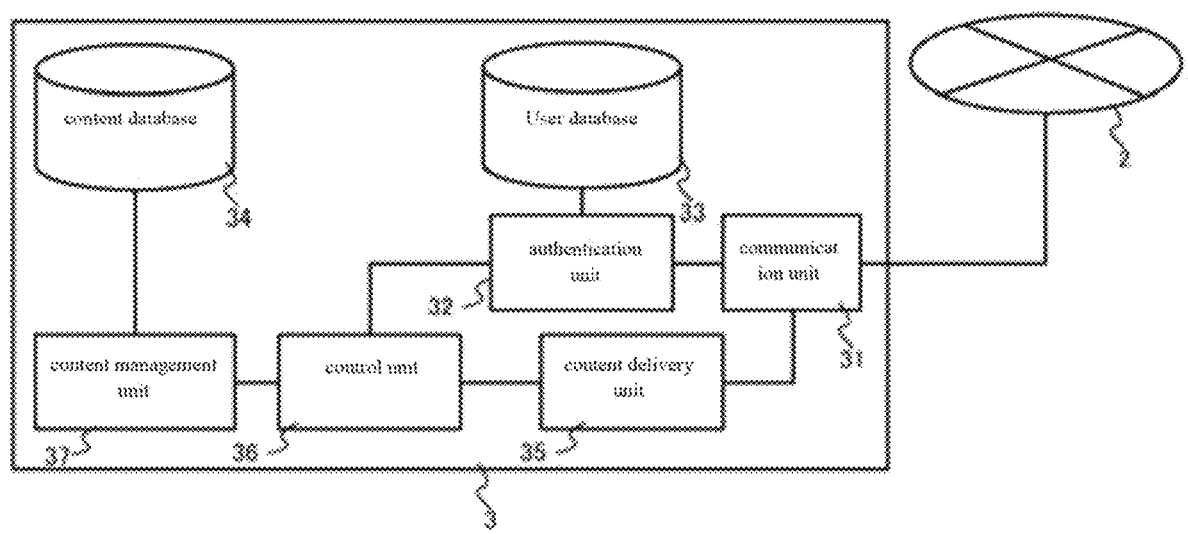
FIG. 2B is a block diagram showing the internal structure of the content management server.

FIG. 1 is a block diagram showing the overall configuration of a system for early detection and prevention of mild dementia according to the present embodiment. FIG. 2A is a block diagram showing the modules related to a function for early detection and prevention of mild dementia that is virtually constructed on a CPU of an information processing terminal according to the present embodiment, FIG. 2B is a block diagram showing the internal structure of the content management server. The "Module" used in the description indicates a functional unit for achieving a predetermined operation constituted by hardware such as a device or equipment, software having the function, or a combination of these.

As shown in the figure, the system for early detection and prevention of mild dementia is a mechanism to carry out check and training for early detection and prevention of mild dementia using information processing terminal 1 that can import the required content and information to the information processing terminal 1 through communication network 2 by connecting to the content management server 3. Content management server 3 and information processing terminal 1 (1a-1c) used by the users are arranged in the communication network 2.

Communication network 2 is a distributed communication network (IP network) that mutually connects various communication lines (telephone and ISDN lines, ADSL line, public lines such as optical communication line, leased lines, and wireless communication network of 3G and 4G) using a communication protocol TCP/IP, this communication network 2 in addition to the Internet, includes LAN such as intranet (intra-company network) based on VPN, 10BASE-T, 100BASE-TX and home networks are also included. Communication network 2 can be connected through wired connection or Wifi communication, for example, Wifi router and wireless LAN router can be used as access point and information processing terminal 1 that is capable of wireless communication can be connected to perform two way communication with the content management server 3 and information processing terminal 1.

(Information Processing Terminal)

As shown in FIG. 1, the information processing terminal 1 includes CPU 11 that performs arithmetic processing, memory 12 that temporarily stores data, communication I/F 13 that performs external communication through communication network 2 and storage device 14 that stores data. In the present embodiment, CPU 11, memory 12, communication I/F 13, storage device 14, output interface 15, and input interface 16 are connected through the CPU bus 1a and data can be mutually transferred.

Communication I/F 13 is a module that communicates with the content management server 3 through the communication network 2, and a publicly known device can be used. Wired communication is possible by connecting a LAN cable or telephone line for internal or external lines to communication I/F 13, and wireless communication is possible by connecting communication chip of Wifi and 3G lines or a cellular phone.

Storage device 14 is a device that stores data on a recording media and read out the data in response to requests from various devices, for example, hard disk drives (HDD), solid state drives (SSD), and memory cards can be used as the storage device. In the storage device 14, OS (Operating System) and various programs such as stereoscopic image content, various programs for early detection and prevention of mild dementia of the present embodiment, programs for various applications installed in the terminal, personal information of the user, and device identification information (ID) of the terminal are stored.

Output interface 15 and input interface 16 is connected to CPU bus 1a, while the incoming user operation signal from input interface 16 is input to the CPU through CPU bus 1a, and information related to the operation for each unit is output from each output device and displayed through CPU bus 1a and output interface 15.

Speaker 5a that outputs sound and a liquid crystal display of a touch panel 5b that outputs images are connected to output interface 15, and mouse 6a, keyboard 6b, touch panel 5b to input user operation such as pointing operation and text input, microphone 6c to input voice, camera 6d to input images, EEG detection device 61 to detect electroencephalogram is connected to the input interface 16. In the present embodiment, the LCD touch panel is superimposed with the liquid crystal display that displays images and touch panel to perform input touch operations. Output interface 15 displays stereoscopic images and GUI according to various programs executed by application execution unit 111 on touch panel 5b.

EEG detecting device 61 is a head set type device that detects the EEG of the observer and outputs electroencephalogram signals corresponding to the EEG and is equipped with an electrode pad 61a and tip 61b to measure the skin surface potential of the viewer. The electrode pad 61a is arranged so as to contact the forehead of the observer in a state where the head set is attached to the head of the observer. The electrode pad 61a and tip 61b are connected by wires. Tip 61b processes the electroencephalogram signals output from electrode pad 61a with an analog signal processing circuit, AD (analog-digital) conversion circuit, digital signal processing circuit, and transmits the signals through an input interface 16 to the application execution unit 111 on CPU 11.

CPU 11 is a device that performs various arithmetic processing necessary for controlling each unit. CPU 11 executes the application for early detection and prevention of mild dementia according to the present invention in accordance with the content input from input interface 16 based on the application program and setting information stored in memory 12. The system for early detection and prevention of mild dementia of the present invention is virtually constructed as a functional module by executing the application for early detection and prevention of mild dementia on CPU 11.

Specifically, CPU 11 is an arithmetic module that is configured in addition to the CPU with DSP (Digital Signal Processor) processor, memory, and hardware of other electrical circuits, or software of programs having these functions, or by the combination of these, and is a module that virtually constructs various functional modules by appropriately reading and executing the programs and performs process related to image data, operation controls of the units, and various processes for user operation.

In the present embodiment, application execution unit 111, model information acquisition unit 112, and voice recognition unit 113 are constructed in CPU 11. The model information acquisition unit 17 is a module to input information on the type of information processing terminal 1 to the application execution unit 111. The model information acquisition unit 112 is a module that accepts input of information related to the classification of information processing terminal 1, or acquires by reading the information related to the classification from the memory of information processing terminal 1, and application execution unit 111 changes the size, position, and aspect ratio of the image displayed on touch panel 5b based on the information of the type that is input from the model information acquisition unit 112 before the stereoscopic image is displayed as well as changes the position of the reference mark indicating the reference position of the image. The voice recognition unit 113 is a module that recognizes voice and inputs the recognized result to the application execution unit, this module acquires voice data from microphone 6c provided in the terminal and analyzes the type of content by extracting acoustic feature values from the voice data.

In the present embodiment, when the program for early detection and prevention of mild dementia is executed, the operations by the observer is accepted by touch panel 5b, but for example, operation devices such as a mouse 6a or keyboard 6b may be connected by a cable or short-distance communication, and operations by the observer may be accepted based on the operation device.

The application execution unit 111 is a module that executes applications such as general OS, browser software, media viewing application, and is usually realized by a CPU. Specifically, the application execution unit 111, according to the present embodiment, virtually constructs various function modules on the CPU by executing various applications. In the present embodiment, the application execution unit 111 has EEG detection device control unit 111a, synchronization processing unit 111b, stereoscopic vision test execution unit 111c, EEG signal recording unit 111d, test result recording unit 111e, and analysis unit 111f configured on the CPU 11.

The EEG detection device control unit 111a is a module for controlling the operation of the EEG detection device 61 from the information processing terminal 1, and is synchronized with the stereoscopic vision test execution unit 111c through the synchronization processing unit 111b so that the EEG detection device 61 can be operated by linking with the execution of the stereoscopic vision test. The synchronization processing unit 111b is a module that connects and operates the EEG detection device control unit 111a and stereoscopic vision test execution unit 111c and electroencephalogram signals recorded by the EEG detection device control unit 111a from the synchronization processing unit 111b can be linked with various test results recorded by the stereoscopic vision test execution unit 111c, this enables the analysis unit 111f to analyze the correlation between the electroencephalogram signals and various test results that are recorded.

Stereoscopic vision test execution unit 111c executes various programs relating to early detection and prevention of mild dementia, and is a module that displays stereoscopic image contents and GUI on touch panel 5b and performs arithmetic processing such as visual acuity measurements. EEG signal recording unit 111d is a module that chronologically records various electroencephalogram signals acquired from the EEG detection device 61 in the storage device 14. Depending on the detected values of EEG signals, timing and intensity of stimulation from the stereoscopic viewing program executed by the stereoscopic vision test executing unit 111c is adjusted in real time in the synchronization processing unit 111b and stimulus for cognitive functions based stereoscopic vision may be more effectively performed.

The recorded electroencephalogram includes delta waves (4 Hz to 0.5 Hz), theta waves (8 Hz to 4 Hz), alpha waves (14 Hz to 8 Hz), beta waves (38 Hz to 14 Hz), and gamma waves (26 Hz to 70 Hz). Delta waves are detected during healing, sleeping, state of deep sleep, or unconscious state, theta waves is related to meditation and intuition, and memory skills, and is detected when the brain waves are in a state suitable for memorizing and learning. Alpha waves are detected in the state of increased awareness level when mental activity is active during relaxation, visualization, creativity and relaxed state, and state exhibiting problem solving and concentration can be detected, beta waves are detected when in a state of tension such as warning, concentration, cognitive ability, rationally solving problems, and while paying attention. Gamma waves have relevance to prediction, clarity, perspective and is detected when concentration has increased.

Test result recording unit 111e is a module that records various test results output by the stereoscopic vision test execution unit 111c in storage device 14. Synchronization processing unit 111b links data recorded by the EEG signal recording unit 111d and test result recording unit 111e and history of user operations during the test included in the test results and relationship between the change in accuracy and EEG signals can be recorded.

Analysis unit 111f is a module that links and analyzes the test result recorded by the stereoscopic viewing program executed by the stereoscopic vision test execution unit 111c of the application execution unit 111 and the EEG signals recorded by the EEG signal recording unit 111d.

Figure 21A:
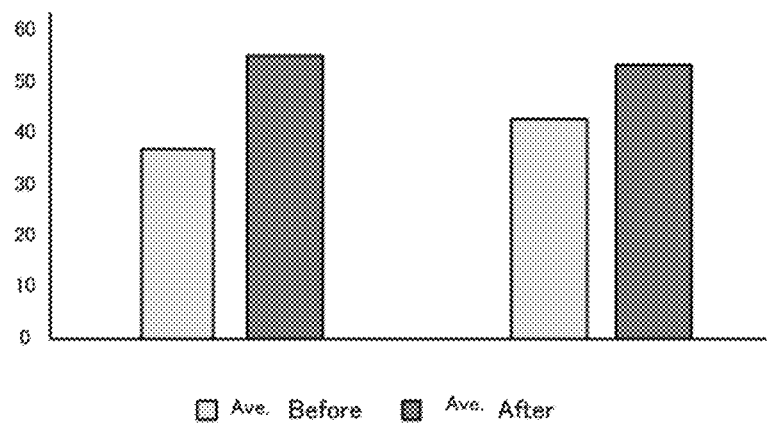
FIG. 21A, FIG. 21B is an explanatory diagram showing an example of the display information indicating the measurement results of the electroencephalogram signals in the system for early detection and prevention of mild dementia according to the embodiment.
Figure 21B:
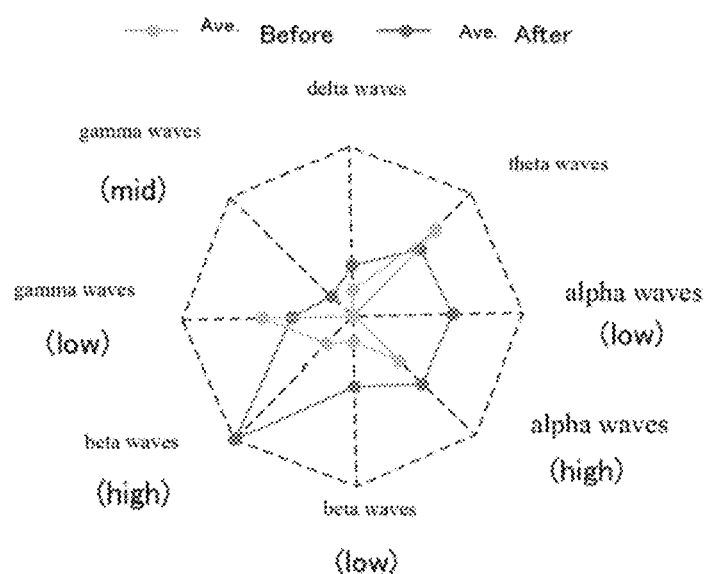

For example, analysis unit 111f executes the stereoscopic viewing programs such as the check and training programs 1 to 5 described above, records the accuracy of user operations in each test as test results and chronologically records the detection values of various EEG during the execution of programs 1 to 5, analyzes the average value, maximum value, minimum value, start value, end value, temporal change, and distribution in each test and associates the test results with the detected value of EEG signal by each stereoscopic program and generates graphic display information such as charts, graphs, and radar chart that indicates the correlation. With this, test results and detection values of EEG signal can be displayed for comparison and impairments such as dementia can be identified with higher accuracy. The test results analyzed and calculated by analysis unit 111f and EEG analysis results as shown in FIG. 21A, FIG. 21B is output on the display or from the printer through output interface 15 as display information including graphics of graph and radar charts.

When various programs according to the present invention are executed in the application execution unit 111, a stereoscopic image constituted by generating a convergence angle and parallax between the left eye image and the right eye image corresponding to the left and right eyes of the observer is displayed on the screen, and the focal point with respect to the eyes of the observer is guided towards and away from the observer by changing the convergence angle and parallax of the stereoscopic image. A good stereoscopic image can be observed as only the image for the right eye is at the focal point of the right eye and only the image for the left eye is at the focal point of the left eye.

Application execution unit 111, when displaying the right eye and left eye images on touch panel 5b, reduces the size of the image to maintain the aspect ratio and displays on touch panel 5b. The right eye image and left eye image can be reduced depending on the model of the information processing terminal. The application execution unit 111 changes the size, position, and aspect ratio as well as the position of the reference mark indicating the reference position of the image displayed on touch panel 5b based on the information of the type that is input from the model information acquisition unit 112 before the stereoscopic image is displayed. Specifically, when a position adjustment program recorded in storage device 14 and the position adjustment program is executed by the application execution unit 111, stereoscopic images can be displayed at an appropriate position depending on the model of the information processing terminal 1. The program to scale the display range of the stereoscopic image is stored in the image storage device 14 and when the display range is changed by the user, the application execution unit 111 scales the stereoscopic image and changes the display range based on the operations of input interface 16.

(Content Management Server)

The content management server 3 is a content server device that collects and distributes contents, performs authentication process and customer management of observers who are registered users, and manages all types of programs and image content for early detection and prevention of mild dementia. The content management server 3 can be realized by a server computer that transmits information such as HTML (Hypertext Markup Language) files, image files, music files with the documents system of WWW (World Wide Web) or a software with the same functions, contents such as images can be collected and this information can be transmitted through an IP network of Internet based on the request from client software in the present embodiment.

Specifically, the content management server 3 is equipped with a communication unit 31 for connecting to the communication network 2, authentication unit 32 for authenticating user access, content delivery unit 35 for transmitting content, content management unit 37 that manages input and output to the database, and a control unit 36 that controls the operations of all modules. User database 33 and content database 34 are connected to the content management server 3.

Communication unit 31 is a communication device that transmits content data by sending and receiving packet data and is equipped with a function to send and receive data with the programs executed in the information processing terminal 1. Content distribution unit 35 is a module that transmits the content data read by the content management unit 37 to the information processing terminal 1 of the user authenticated by the authentication unit 32 through communication unit 31.

Authentication unit 32 is a module for determining access permission to a user, and authenticates by comparing with the authentication information collected in the user database 33. User database 33 has information on the name, telephone number, and credit card associated with the customer ID, information on the check and training results of the program for early detection and prevention of mild dementia, and history information on the content used.

Contents database 34 is an information data storage device that can be accessed from communication network 2 and for example, the device may be composed of a large-capacity hard disk. Information accumulated in the content database 84 includes content data and index data that associates type (music, voice, image, and character string)

and file format of the content data, attributes (genre and age) of the content data for the data ID that identifies each content data.

Content database 84 reads and writes the content data based on the control of content management unit 37. As control for content database 84, a type that calls the content data by an identifier (an address or a file name in the database) that specifies the content data, or a type that calls the content data by specifying the content data based on the type, file format or attributes, and information in the index data can be mentioned.

Content management unit 37 is equipped with the function to accept data uploaded through communication network 2, and to collect and manage the uploaded data as content. Specifically, content management unit 37 associates the information including age of the subject shown in the image with the uploaded image and stores in the content database 34. Content management unit 37 is also equipped to function as a content selection unit for retrieving the delivery request that includes the age of the observer being tested from information processing terminal 1 through communication unit 31 and selects the image matching with the age of observer included in the delivery request from content database 34.

Content delivery unit 35 is a module that delivers the image selected by the content management unit 37 to the information processing terminal 1, and delivers the content data to the user terminal through the communication path established by communication unit 31. Content distribution unit 35 is a module that converts content data into packets or decodes packet data into content data.

(Configuration of the Stereoscopic Image Display Device)

Figure 15A:
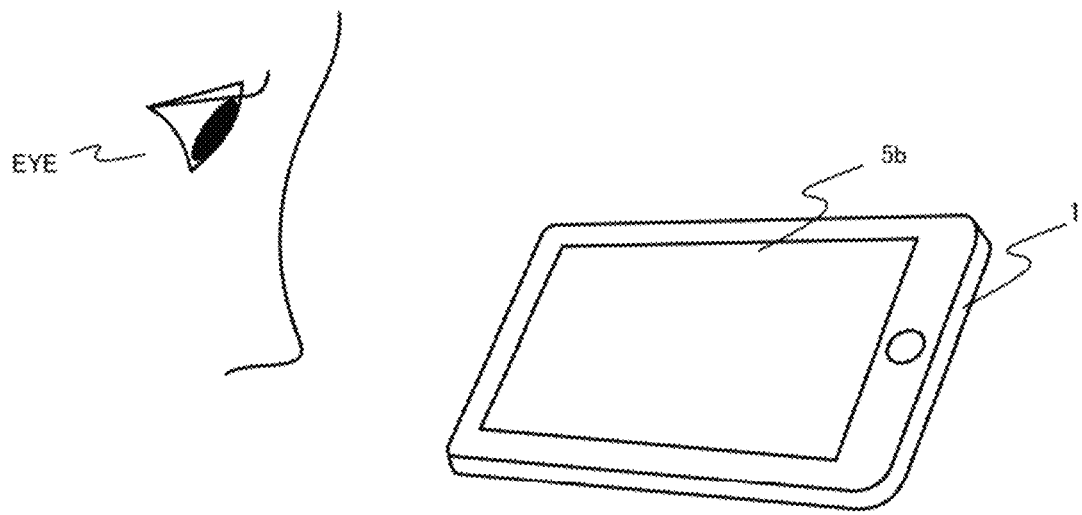
FIG. 15A, FIG. 15B is an explanatory diagram showing the state of observing the display of the information processing terminal with the naked eye according to the embodiment.
Figure 15B:
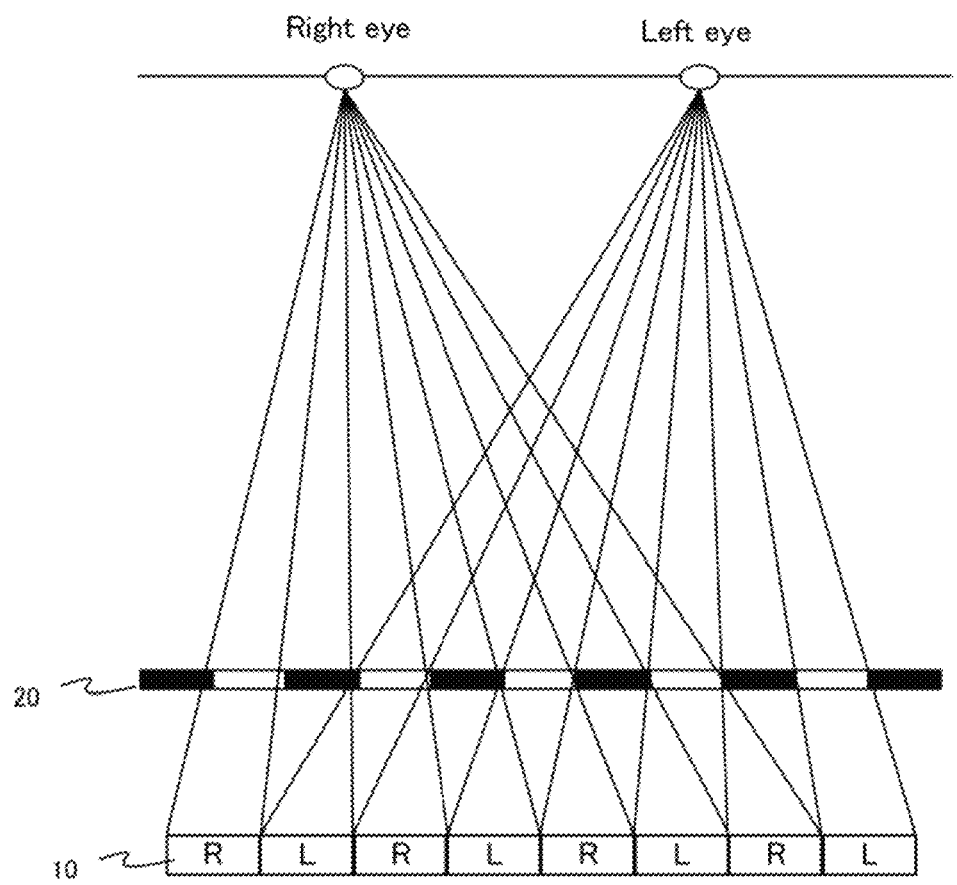

FIG. 15A, FIG. 15B is a diagram showing the parallax barrier and components of the stereoscopic image display device that includes the parallax barrier according to the embodiment. In the present embodiment, the stereoscopic image display device is included in touch panel 5b. Stereoscopic image display device is one example to display stereoscopic images, and the present invention is not limited to this device and Various stereoscopic image display devices such as 3D smart phones not requiring glasses, other methods of parallax barrier, and other lenticular.

As shown in FIG. 15B, the stereoscopic image display device of the present embodiment includes the display module 10 with left image (L) and right image (R) arranged alternately in the horizontal direction facing the vertical direction corresponding respectively to the left and right eyes based on the parallax barrier method, and a bar-shaped blocking film facing the vertical direction called barrier 20 provided at the front end. In such a stereoscopic image display device, the display module 10 and barrier 20 is arranged such that the light corresponding to the left image (L) is incident only on the left eye and light corresponding to the right image (R) is incident only on the right eye, and the stereoscopic effect is felt by separating and viewing the 2 left and right images (L, R). With this, as shown in FIG. 15A, a stereoscopic image can be seen on simple display with naked eyes without attaching any special devices.

Figure 16A:
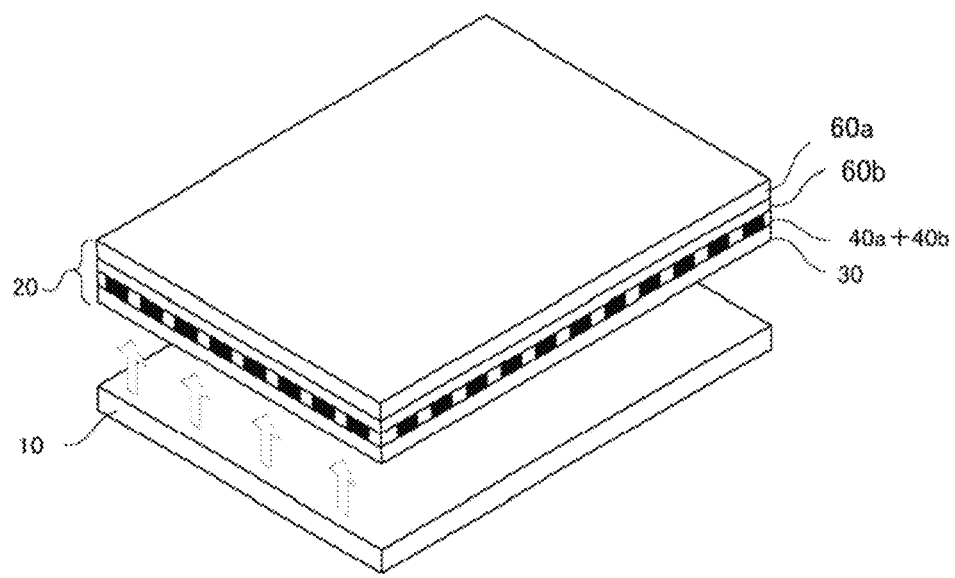
FIG. 16A, FIG. 16B is an explanatory diagram showing the parallax barrier and components of the stereoscopic image display device that includes the parallax barrier according to the embodiment.

Specifically, as shown in FIG. 16A, the parallax barrier 20 according to the present embodiment includes a lower layer 30, a liquid crystal layer 40a, control unit 40b, upper layer 60b, and polarizing unit 60a. Liquid crystal layer 40a includes pixels arranged in a matrix form of a cell structure so as to form a horizontal or vertical barrier according to the control method, control unit 40b selectively turns on or off each pixel of the liquid crystal layer 40a based on the control method, and controls each pixel of the liquid crystal layer 40a so as to form a horizontal or vertical barrier pattern; Cell structure and specific control method of each pixel included in the liquid crystal layer 40a is described in detail below.

Lower layer 30 is formed between the liquid crystal layer and display module to arrange the liquid crystal layer and control unit at a position separated by a predetermined distance from the display module. Upper layer 60b is formed at the upper end of the liquid crystal layer to arrange the liquid crystal layer and control unit. Polarizing section 60a controls the polarization angle of light emitted from the display module and passes through the lower layer, liquid crystal layer and upper layer, and enables visualization of the barrier by the barrier pattern formed on the liquid crystal layer. Since the parallax barrier of the present embodiment has polarizing portion 60a only at the upper end of upper layer 60b unlike conventional parallax barrier in which the polarizing unit 60a is positioned at the upper end of upper layer 60b and lower end of lower layer 30, decrease in luminance of light generated by passage through polarizing unit 60a can be reduced.

Parallax barrier 20 and the stereoscopic image display device that includes the barrier of the present embodiment forms the barrier pattern using a liquid crystal panel such as a TN-LCD or STN-LCD, and 2D image can be viewed with the barrier turned off in the 2D mode and 3D image can be viewed with the barrier turned off in the 3D mode. The screen in the vertical direction can be viewed by driving the pixels in the vertical direction to turn on the barrier in the vertical direction, and the stereoscopic image can be viewed by driving the pixels in the horizontal direction to turn on the barrier in the horizontal direction. That is, the barrier and the stereoscopic image display device that includes the barrier of the present embodiment forms enables switching between 2D and 3D mode and between horizontal and vertical directions.

Figure 16B:
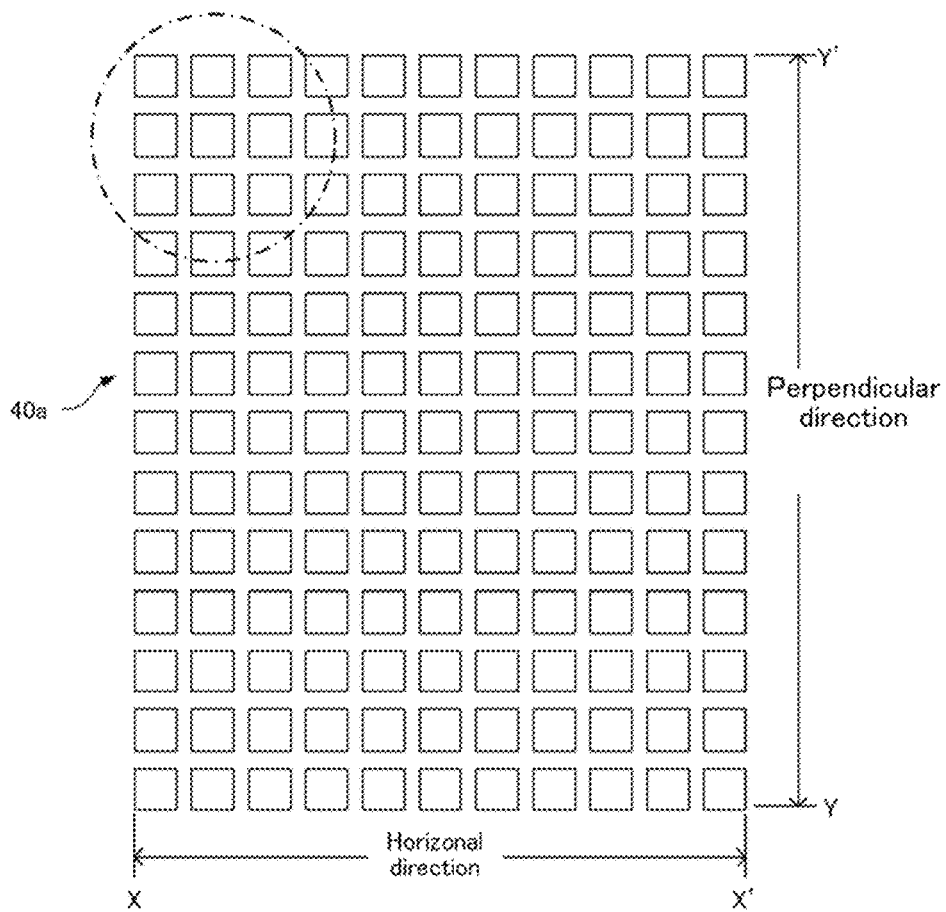

FIG. 16A, FIG. 16B is an illustrative diagram showing the barrier pattern structure of the liquid crystal layer 40a in cell units for the present embodiment. Liquid crystal layer 40a alternately arranges the barriers in cell units for different specifications in the horizontal direction (X-X') and vertical direction (Y-Y') to form a pattern structure of cell units. As shown in FIG. 16, when the pixels forming a barrier in the horizontal direction is referred to as the cell column of the first horizontal direction, cell column of the second horizontal direction, cell column of the third horizontal direction, first pixel in which horizontal×vertical is a×c, second pixel in which horizontal×vertical is b×c are sequentially arranged in the cell column of the first horizontal direction, and third pixel in which horizontal×vertical is a×d, and fourth pixel in which horizontal×vertical is b×d are sequentially arranged in the cell column of the second horizontal direction. Values of a, b, c, and d are standard values calculated based on the specifications of the display module, and are determined such that the barrier thickness and interval can be accurately displayed.

Cell columns in the third horizontal direction are arranged in the same structure as the cell columns in the first horizontal direction and cell columns in the fourth horizontal direction are arranged in the same structure as the cell columns in the second horizontal direction. That is, the barrier base of the present embodiment has 2 horizontal cell columns with mutually different structures arranged alternately in the vertical direction.

(Information on the Overall Operations of the Main System)

The early detection and prevention method of the present invention can be implemented by operating the early detection and prevention system that has the above configuration.

Figure 20:
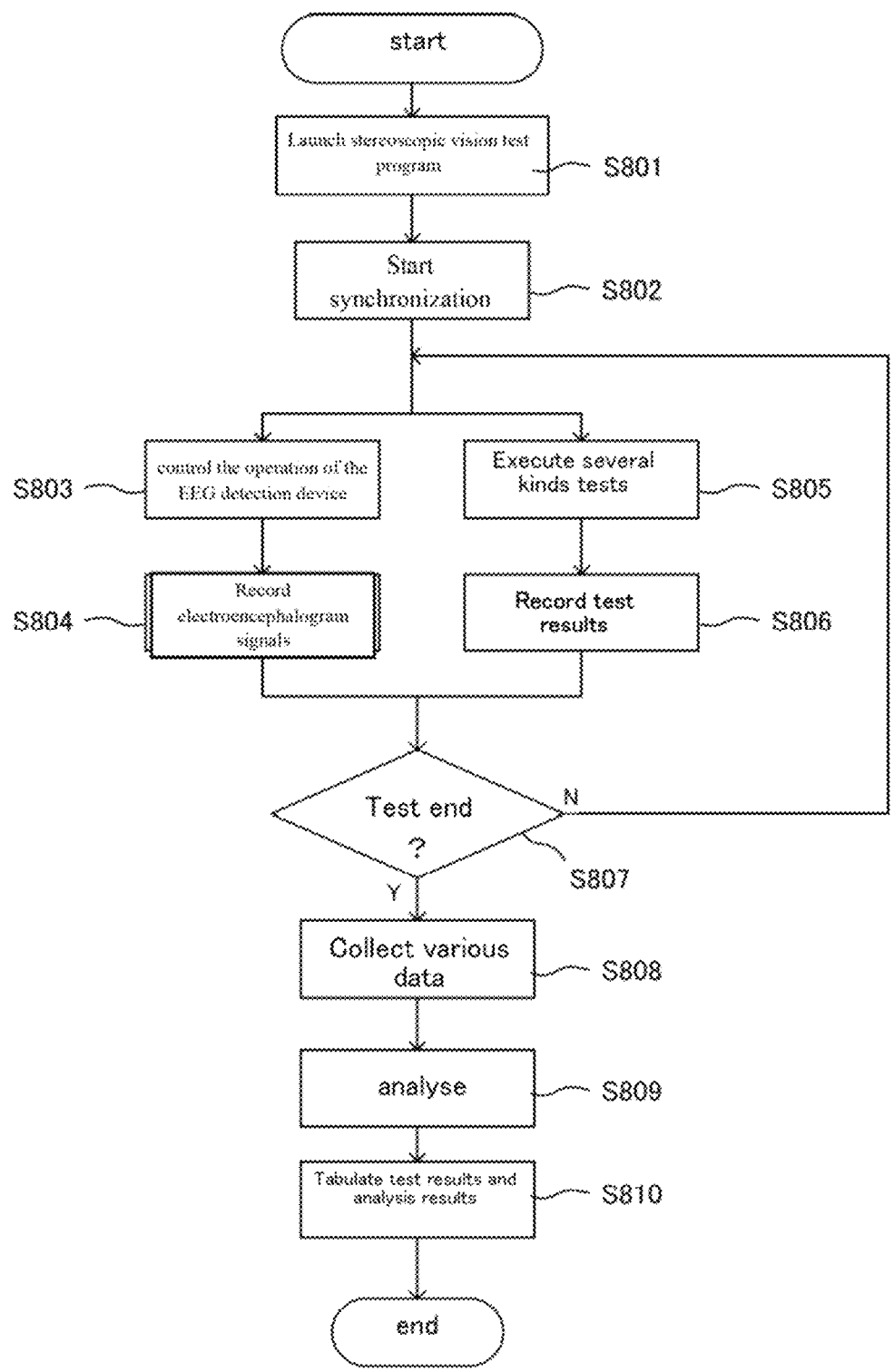
FIG. 20 is a flowchart showing the overall operation of a system for early detection and prevention of mild dementia according to the embodiment.

FIG. 20 is a flowchart showing the operation of the early detection and prevention system according to the present embodiment.

When the stereoscopic vision test program is first launched (S801), process of synchronization with the EEG detection device 61 starts (S802). Specifically, EEG detection device control unit 111a controls the operation of the EEG detection device 61 from the information processing terminal 1 (S803), synchronizes with the stereoscopic vision test execution unit 111c through the synchronization processing unit 111b, and records electroencephalogram signals from the EEG detection device 61 (S804) by linking with the execution of the stereoscopic vision tests (S805).

More specifically, stereoscopic vision test execution unit 111c executes various programs relating to early detection and prevention of mild dementia, and displays stereoscopic image contents and GUI on touch panel 5b and performs arithmetic processing such as visual acuity measurements. In conjunction with this, EEG signal recording unit 111d chronologically records various electroencephalogram signals acquired from the EEG detection device 61 in the storage device 14. Test result recording unit 111e records various test results output by the stereoscopic vision test execution unit 111c in storage device 14 (S806). Synchronization processing unit 111b links data recorded by the EEG signal recording unit 111d and test result recording unit 111e and history of user operations during the test included in the test results and can record the relationship between the change in accuracy and EEG signals.

During calculation process of visual acuity measurement, depending on the detected values of EEG signals, timing and intensity of stimulation from the stereoscopic viewing program executed by the stereoscopic vision test executing unit 111c may be adjusted in real time with the synchronization processing unit 111b.

After continuing various tests until all tests are completed ("N" in S807), electroencephalogram signals and various test results recorded by the stereoscopic vision test execution unit 111c are linked and collected (S808), next analysis unit 111f analyzes the correlation between the recorded electroencephalogram signals and various test results (S809). More specifically, the test results recorded by the stereoscopic viewing program executed in the stereoscopic vision test execution unit 111c of the application execution unit 111 and EEG signals recorded by the EEG signal recording unit 111d is linked and analyzed by analysis unit 111f.

In the present embodiment, stereoscopic viewing programs such as the check and training programs 1 to 5 that will be described later is executed to record the accuracy of user operations in each test as test results and chronologically record the detection values of various EEG during the execution of programs 1 to 5, analyze the average value, maximum value, minimum value, start value, end value, temporal change, and distribution in each test, associate the test results with the detected value of EEG signal by each stereoscopic program, and generate graphic display information such as charts, graphs, and radar chart that indicates the correlation (S810). The test results analyzed and calculated by analysis unit 111f and EEG analysis results as shown in FIG. 21A, FIG. 21B is output on the display or from the printer through output interface 15 as display information including graphics of graph and radar charts. This enables test results and detection values of EEG signal to be displayed for comparison.

(Information on Various Stereoscopic Viewing Programs)

Next, various stereoscopic viewing programs executed in the application execution unit 111 described above will be explained in detail.

(1) Check and Training Program 1

Figure 3:
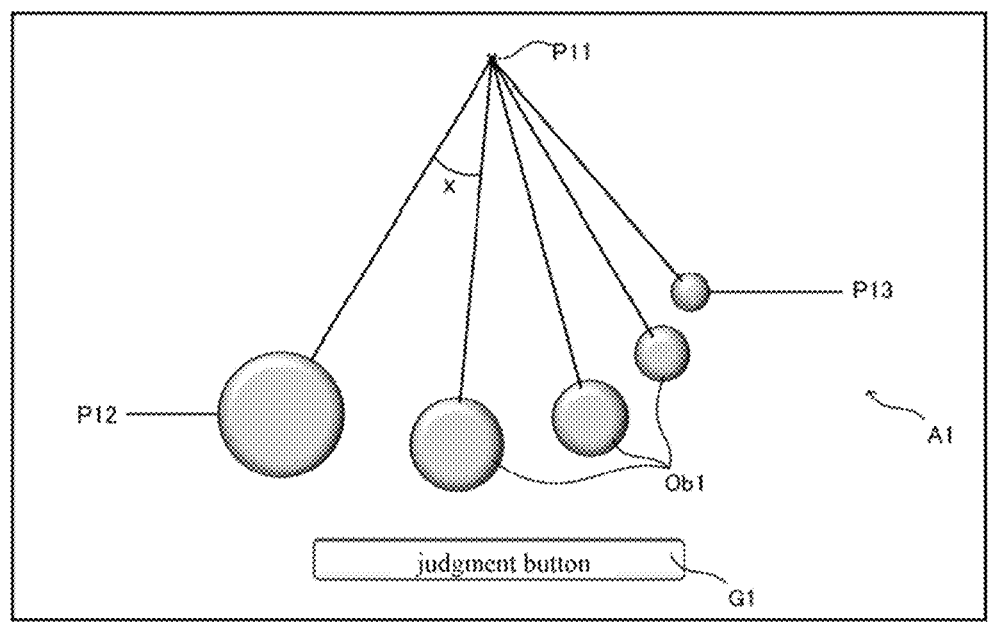
FIG. 3 is an explanatory diagram showing the screen configuration of the check and training program 1 according to the embodiment.
Figure 4:
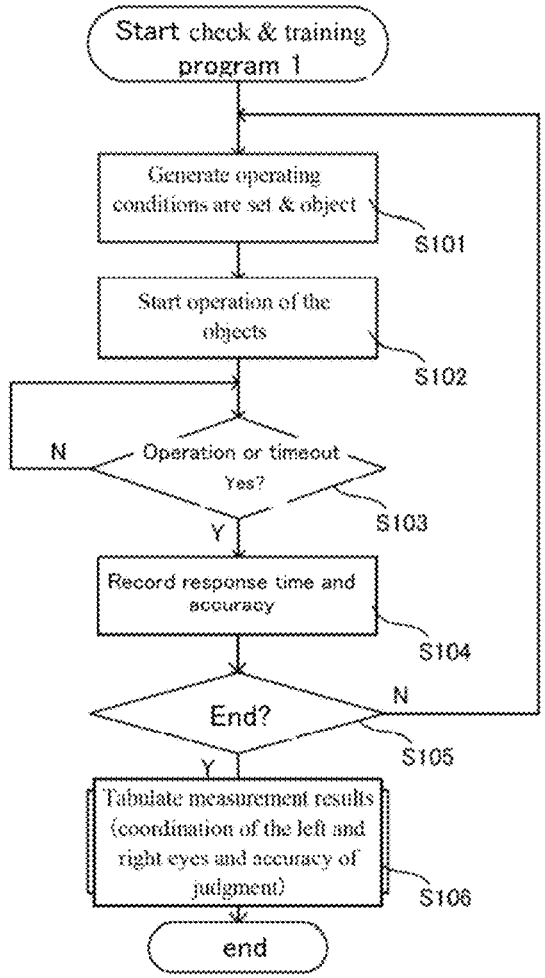
FIG. 4 is a flowchart showing the operations of the check and training program 1 according to the embodiment.

FIG. 3 is an explanatory diagram showing the screen configuration of the check and training program 1 and FIG. 4 is a flowchart showing the operations of the program. In the check and training program 1, a pendulum is used to measure the coordination of the left and right eyes and accuracy of judgment, and correctness of judgment and action time is checked with the activity status of the frontal lobe and eye movements.

More specifically, in schizophrenia, function of the frontal lobe deteriorates as the number of nerve cells decreases in the frontal lobe, hippocampus, and surrounding areas of the brain, and deterioration of the function can be clearly experienced with tests that specifically check the movement of frontal lobe. For example, there is a tendency that the movement of eyes becomes awkward or the visual point does not move much and gets fixed when the observer is asked to view a specific figure. For this reason, in this program, coordination of the left and right eyes and accuracy of judgment is diagnosed by expressing judgment accuracy of pendulum reciprocating points P 12, P 13 using stereoscopic vision with ±values.

In the present program, a stereoscopic image area A1 is generated in which a stereoscopic image constituted by generating a convergence angle and parallax between the left eye image and right eye image is displayed and pendulum object Ob1 swinging in the virtual space constructed within the stereoscopic image area A1 is displayed. At the bottom of the stereoscopic image area A2, the judgment button G1 which is the user interface is displayed. The pendulum object Ob1 swings between the reciprocating points P12 and P13 centered around an arbitrary center point P11 in the virtual space.

During testing, user is made to press judgment button G1 when object Ob1 reaches the reciprocating points P12, P13 (any one or both points). The difference between the timing at which object Ob1 actually reaches the reciprocating point P12 or P13 and when the user operates judgment button G1, and accuracy of the user operation is recorded as the test results.

The above-described check and training program operates as follows.

First, when the program is started, operating conditions are set and the object for executing the operation according to the set conditions is generated in step S101.

The operation settings for the present embodiment is as follows.

The angle values of amplitude X of the pendulum can be changed from the default of 45 degrees and 90 degrees towards the front and back in steps of ±5 degrees.

The period of the pendulum is 2.5 seconds by default and can be changed in steps of ±0.5 seconds.

Diameter, color, thread length (swinging radius of pendulum), background color (side by side still images for image replacement) can also be set.

Number of measurements can be set to 3 times by default and can be set any number.

Time log from start to end is converted into data.

Judgment can be set in 5 stages of A, B, C, D and E.

Swing width (front and back side) is set to 60 degrees by default and can be changed by ±angle input.

Camera setting is a cross method with vertical 0 point, and ±values can be input for the camera interval.

Next, operation of the objects starts in step S102. This operation starts automatically after operation conditions are set or with start instructions based on user operations. Step S103, loop process ("N" in S103) for user operation (or timeout). Measurement of elapsed time from when the object has changed starts during this time. Elapsed time is reset when the object changes without user operation and information that the user has not responded is stored as the no-response history.

In step S103, when there is a user operation or after the predetermined time has elapsed ("Y" in S103), process exits the loop process and moves to step S104. In step S104, response time of user and accuracy of operations are recorded. If no-response history is available during the loop process in step S103, object operation at that time, no response time and number of resets are recorded.

Completion of all object operations is determined in step S105, if there is a next operation ("N" in S105), the process proceeds to the next operation and steps S101 to S104 are repeated, and if all the operations have ended ("N" in S103), the process proceeds to step S106. In step S106, measurement results are tabulated, accuracy of coordination between the left and right eye is diagnosed, and results are output.

According to the present program, for example, on a device such as a tablet PC that is capable of 3D display, a pendulum object Ob1 is displayed in the virtual space within the stereoscopic image area and the observer is made to operate the judgment button G1 on recognizing the reciprocating point P12 or P13. Coordination between the left and right eyes and accuracy of judgment can be tested from the difference between the timing at which object Ob1 actually reaches the reciprocating point P12 or P13 and when the user operates judgment button G1, and accuracy of user operations. If this time difference or accuracy exceeds (falls below) a predetermined threshold value, there is a possibility of cognitive impairment, and preventive measures can be taken based on this.

(2) Check and Training Program 2

Figure 5:
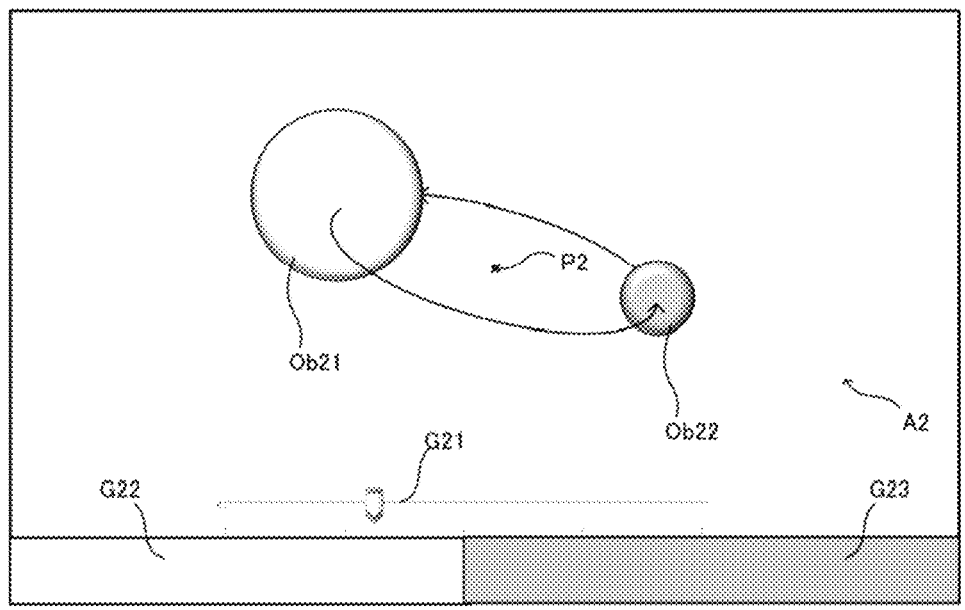
FIG. 5 is an explanatory diagram showing the screen configuration of the check and training program 2 according to the embodiment.
Figure 6:
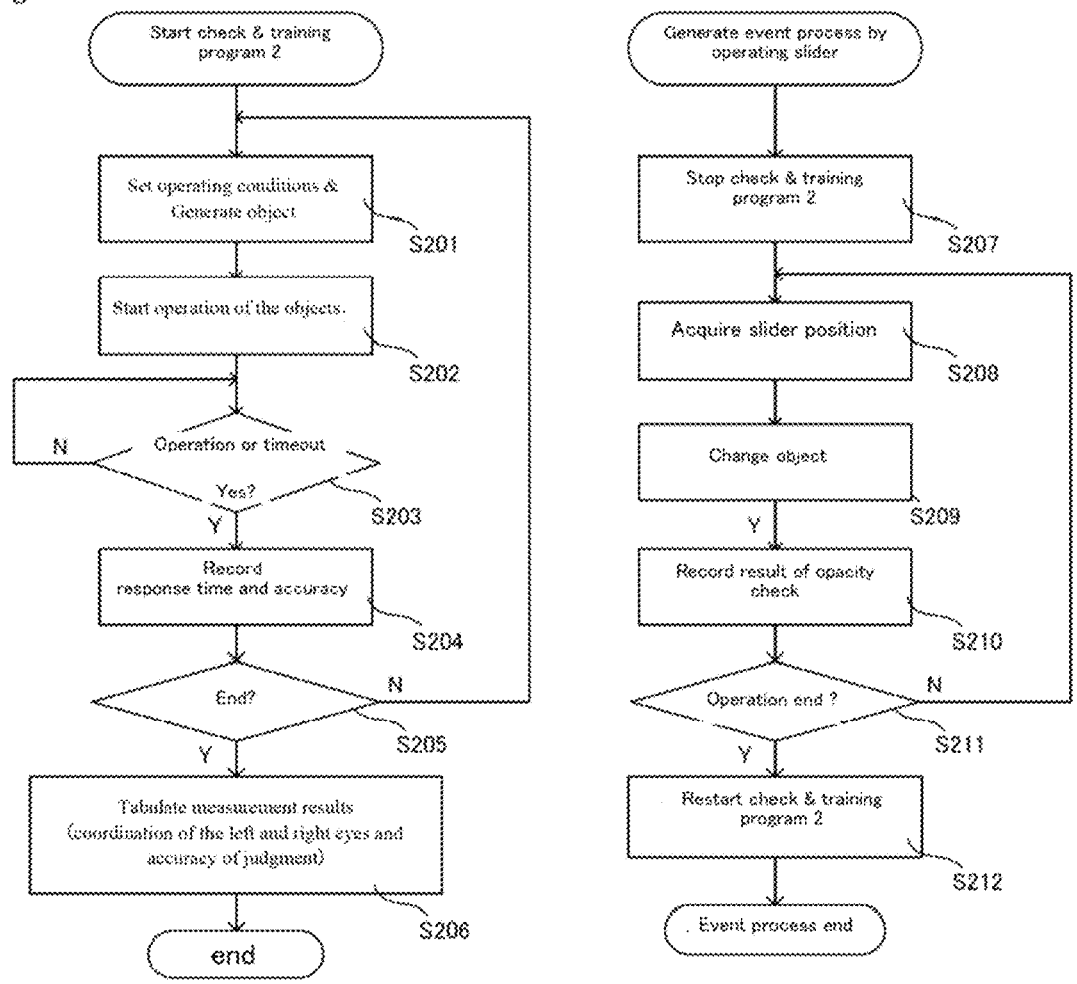
FIG. 6 is a flowchart showing the operations of the check and training program 2 according to the embodiment.

FIG. 5 is an explanatory diagram showing the screen configuration of the check and training program 2 and FIG. 6 is a flowchart showing the operations of the program. In check and training program 2, in addition to diagnoses of spatial recognition ability and situational judgment ability, range of view of observer and opacity based on color adjustment is checked, right and left balance and action time is checked by conducting tests for spatial recognition ability and situational judgment ability.

In the present program, a stereoscopic image area A2 is generated in which a stereoscopic image constituted by generating a convergence angle and parallax between the left eye image and right eye image is displayed and multiple objects Ob21, Ob22 that change positions or orientations in the virtual space constructed within the stereoscopic image area A2 is displayed.

At the bottom of the stereoscopic image area A2, judgment button G22 or G23 which is the user interface is displayed. Judgment buttons G22 and G23 are displayed with colors into which object Ob21 or Ob22 is scheduled to be changed. In the stereoscopic image area A2, slider G21 to slide from the left and right is provided, and can be operated to change the saturation of objects Ob21, Ob22, and judgment buttons G22 and G23 can be changed.

Objects Ob21, Ob22 are rotated at an arbitrary speed around an arbitrary centroid position P2 set in the virtual space and color of one of the objects Ob21 and Ob22 is changed at an arbitrary timing and duration. At this time, rotation radius of objects Ob21 and Ob22 and coordinates of centroid position P2 which is the rotation center are changed, and displayed such that objects Ob21 and Ob22 reach the 4 corners of the stereoscopic image area A1.

During testing, user is made to press judgment button G22 or G23 when color of object Ob21 or object Ob22 changes. The difference between the timing at which objects Ob21, Ob22 changes color and when the user operates judgment button G22 or G23, and accuracy of the user operations are recorded as the test results for spatial recognition ability and situational judgment ability. At the same time, based on the relationship between user action and display position of objects Ob21 and Ob22, areas where the response from the observer has been slow is calculated and visual field range of the observer is also measured. When user operates slider G21, color saturation of the object or user interface that changed due to the slider displacement are measured and color identification and opacity for the user is checked.

The above-described check and training program operates as follows. First, when the program is started, operating conditions are set and the object for executing the operation according to the set conditions is generated in step S201.

The operation settings for the present embodiment is as follows.

Color adjustment to freely change the color of the 2 spheres is provided.

Colors can be made light or dark using the slider bar.

The white and yellow color balls rotate around each other mutual center.

By adjusting the angle of the Z axis, the display can be extended to all the 4 corners of the screen (top, bottom, right and left).

Rotational speed can be adjusted.

Duration of display for red color can be adjusted.

Judgment time can be adjusted.

Number of questions can be changed.

Total number of correct answers, total number of correct answers, correct answers for color identification, correct answers for each area, and response time from time of display.

Results are displayed in 5 steps for overall evaluation, and for individual evaluation total number of correct answers, correct answers for color identification, correct answers for each area, and response time from time of display is considered.

Next, operation of the objects starts in step S202. This operation starts automatically after operation conditions are set or with start instructions based on user operations. Step S203, loop process ("N" in S203) for user operation (or timeout). Measurement of elapsed time from when the object has changed starts during this time. Elapsed time is reset when the object changes without user operation and information that the user has not responded is stored as the no-response history.

In step S203, when there is a user operation or after the predetermined time has elapsed ("Y" in S203), process exits the loop process and moves to step S204. In step S204, response time of user and accuracy of operations are recorded. If no-response history is available during the loop process in step S203, object operation at that time, no response time and number of resets are recorded.

Completion of all object operations is determined in step S205, if there is a next operation ("N" in S205), the process proceeds to the next operation and steps S201 to S204 are repeated, and if all the operations have ended ("N" in S203), the process proceeds to step S206. In step S206, measurement results are tabulated, accuracy of coordination between the left and right eye is diagnosed, and results are output.

In the present program, color identification by observer and opacity of eyeballs can be checked in addition to the check of spatial recognition ability. Color identification and opacity checks can be performed sequentially at any time decided by the user, for example, before or during the test based on the above steps S201 to S205. Specifically, when the slider G21 that is displayed in the stereoscopic image area A2 is operated, event process (interrupt process) is generated and steps S207 to S212 will be executed. If this event process is executed, first, the check and training program 2 is stopped (S207), position of the slider that was operated by the user is retrieved, and color saturation of the object is modified based on slider displacement (S209). Based on the adjustment amount of color saturation of object by user operation, color identification and opacity of the eyeballs of the observer can be diagnosed and the diagnosis results are recorded (S210).

When the user continues operating the slider G21 ("N" of step S211), steps S208 to S210 given above is executed again each time the user operates the slider G21, and diagnosis results of color identification and opacity are updated and recorded, and check and training program 2 is restarted (S212) if the user terminates the operation ("Y" of step S211).

According to the present program, color of multiple objects Ob21, Ob22 that rotate in arbitrary complex orbits are made to change at arbitrary timing and duration, and the observer is made to operate the judgment buttons G22 or G23 on recognizing the change. The spatial recognition ability and situation judgment ability is checked by measuring the time required for the observer to perform the operation from when the object color changes, and accuracy of operations. If this time difference or accuracy exceeds (falls below) a predetermined threshold value, there is a possibility of cognitive impairment, and preventive measures can be taken based on this.

Objects Ob21, Ob22 are displayed up to the 4 corners of the stereoscopic image area A1, and visual field range of the observer can be measured by observing the reaction of the observer and cognitive impairment can be estimated from the width of the visual field.

By changing and adjusting the color saturation of objects Ob21, Ob22 with operation of slider 21 such that the observer can easily see the object, color identification by the observer and opacity of the eyeballs can be detected.

(3) Check and Training Program 3

Figure 7A:
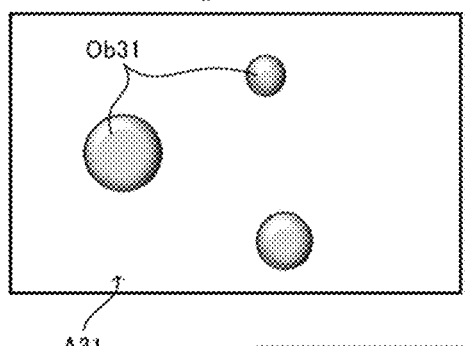
FIG. 7A-FIG. 7C is an explanatory diagram showing the screen configuration of the check and training program 3 according to the embodiment.
Figure 7B:
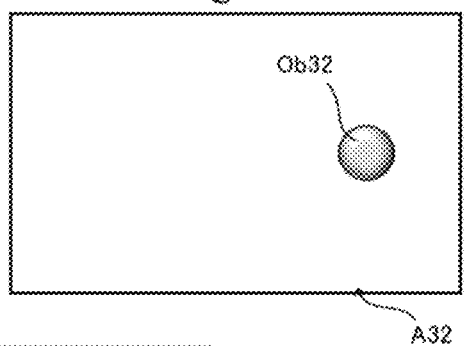
Figure 7C:
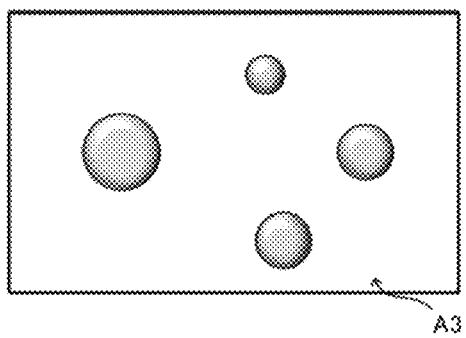
Figure 8:
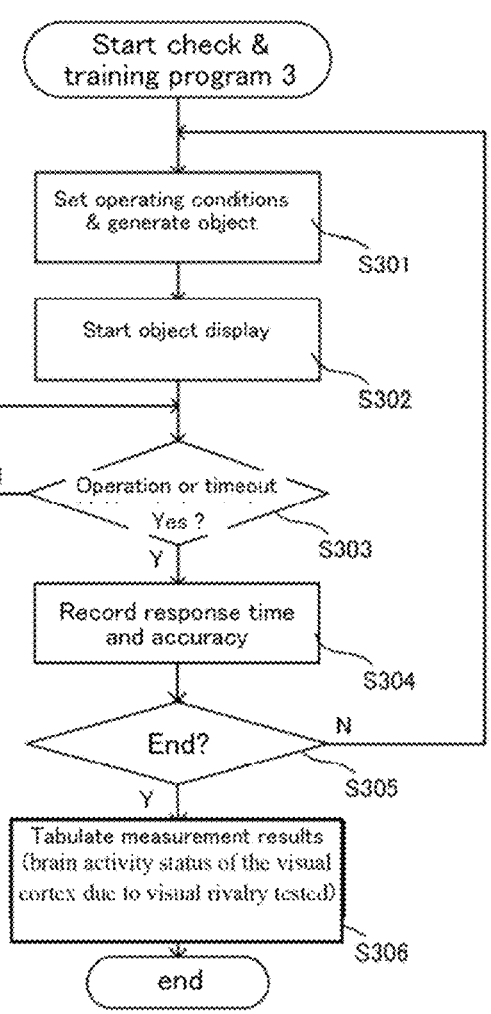
FIG. 8 is a flowchart showing the operations of the check and training program 3 according to the embodiment.

FIG. 7A-FIG. 7C is an explanatory diagram showing the screen configuration of the check and training program 3 and FIG. 8 is a flowchart showing the operations of the program. Check and training program 3 can be used to diagnose the status of brain activity of visual cortex due to visual rivalry. Specifically, by performing stereoscopic vision examination, in addition to correctly rectifying deviation of the position (line of sight) with eyeball muscles (motoneuronal) and action of the brain (sensorineural) to test that there is no double state being viewed, status of brain activity of visual cortex due to visual rivalry can be checked by adding different figures and parallax.

In the present program, left and right image area A3 is generated displaying different number of objects Ob31, Ob32 in the left eye image area A31 and right eye image area A32.

In the present embodiment, convergence angle and parallax are generated between the left eye image and right eye image, and depth (coordinates in the direction of depth) is varied while displaying objects Ob31, Ob32. In the present embodiment, even though the process of changing the depth based on 3D display is performed, for example, different number of objects can be simply displayed on the left and right in a 2D display.

In the left and right image area A3, objects Ob31, Ob32 are selected with a user interface such as a touch screen. Degree of match/mismatch between the coordinates where objects Ob31, Ob32 are displayed and coordinates of the touch operation is recorded as test results of the activity status of visual cortex in the brain due to visual rivalry.

The above-described check and training program operates as follows.

First, when the program is started, operating conditions are set and the object for executing the operation according to the set conditions is generated in step S301.

The operation settings for the present embodiment is as follows.

In the 2D mode, normal stereo test is performed and in the 3D mode, depth is set as back, screen, and front. In this check program, depth is added to the normal stereo vision test to check the relationship between cognitive ability and left and right cerebral vision.

The marks to be displayed can be selected from shapes, numbers, alphabets, Kanji, Hiragana, Katakana, animals, plants, fish, food, vegetables, fruits, and vehicles.

Next, operation of the objects starts in step S302. This operation starts automatically after operation conditions are set or with start instructions based on user operations. Step S303, loop process ("N" in S303) for user operation (or timeout). Measurement of elapsed time from when the object has changed starts during this time. Elapsed time is reset when the object changes without user operation and information that the user has not responded is stored as the no-response history.

In step S303, when there is a user operation or after the predetermined time has elapsed ("Y" in S303), process exits the loop process and moves to step S304. In step S304, response time of user and accuracy of operations are recorded. If no-response history is available during the loop process in step S303, object operation at that time, no response time and number of resets are recorded.

Completion of all object operations is determined in step S305, if there is a next operation ("N" in S305), the process proceeds to the next operation and steps S301 to S304 are repeated, and if all the operations have ended ("N" in S303), the process proceeds to step S306. In step S306, measurement results are tabulated, status of brain activity of visual cortex due to visual rivalry is diagnosed, and results are output.

According to the present program, brain activity status of the visual cortex due to visual rivalry can be tested by displaying different number of objects for the left eye image and right eye image in the left and right image areas.

(4) Check and Training Program 4

Figure 9:
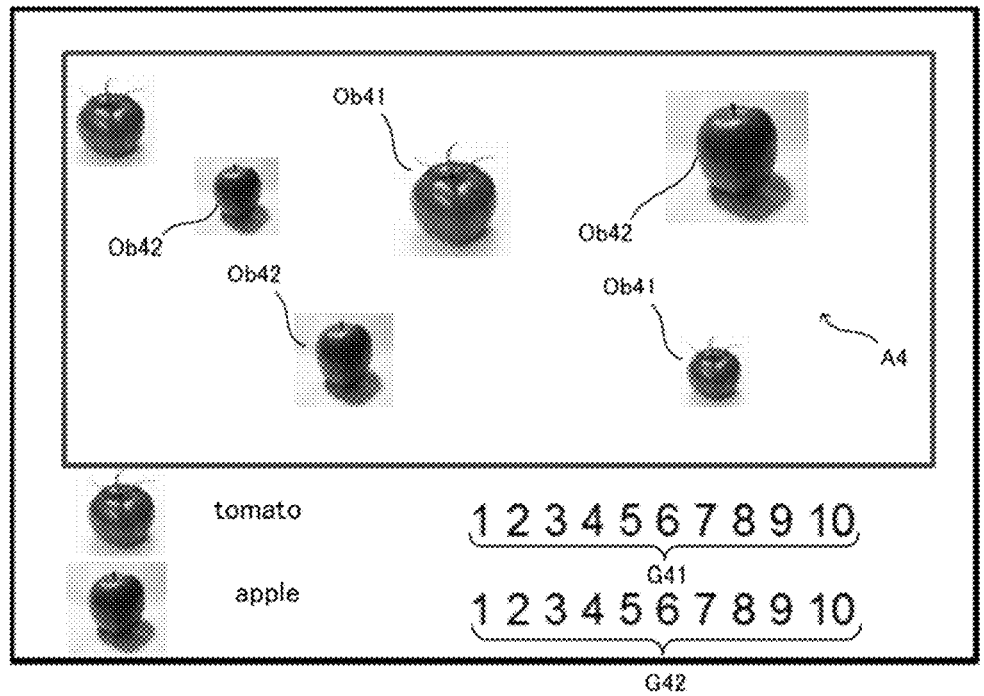
FIG. 9 is an explanatory diagram showing the screen configuration of the check and training program 4 according to the embodiment.
Figure 10:
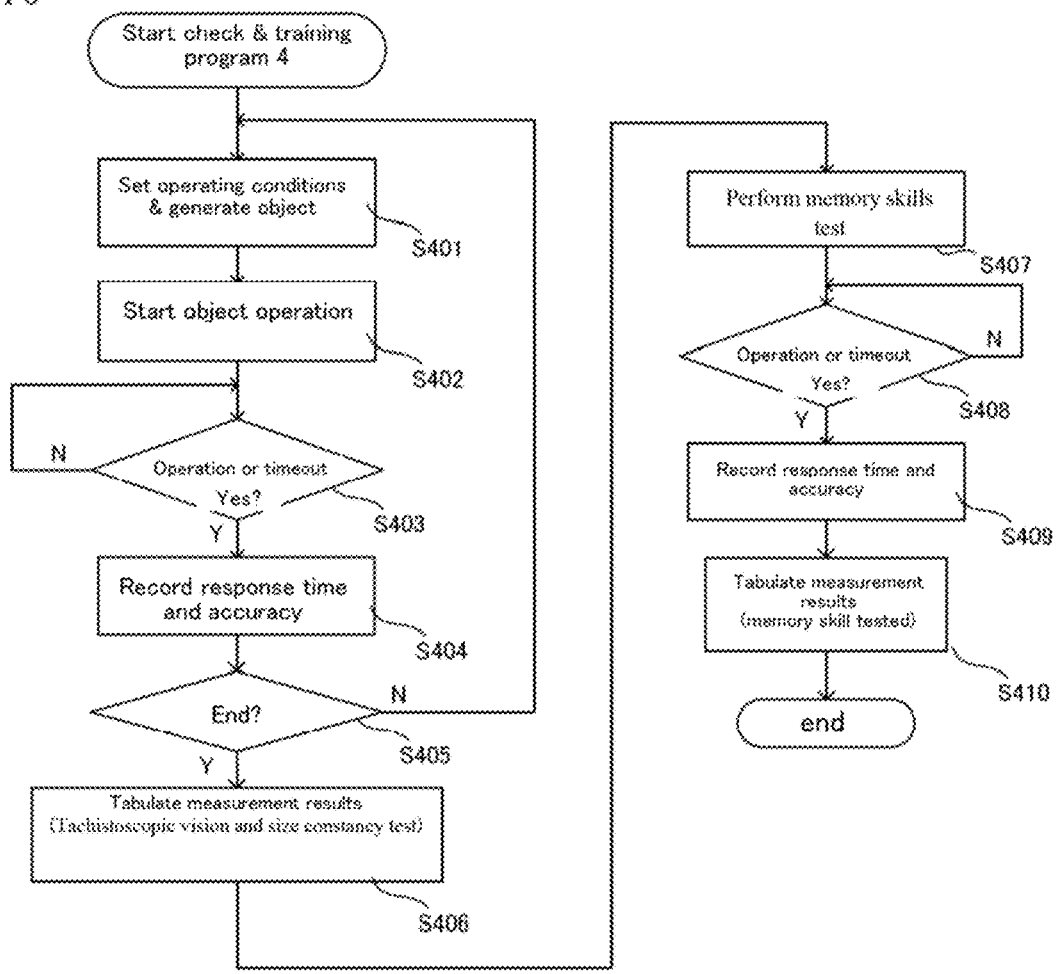
FIG. 10 is a flowchart showing the operations of the check and training program 4 according to the embodiment.

FIG. 9 is an explanatory diagram showing the screen configuration of the check and training program 4 and FIG. 10 is a flowchart showing the operations of the program. Check and training program 4 can be used to diagnose tachistoscopic vision, size constancy, and memory skills. Specifically, as parallax information is available, in addition to general tachistoscopic vision, size constancy checks are performed and along with checking the activity state of cerebrum and visual cortex, memory skills of the brain is checked using tachistoscopic vision.

In the present program, a stereoscopic image area A4 is generated in which a stereoscopic image constituted by generating a convergence angle and parallax between the left eye image and right eye image is displayed and multiple objects Ob41, Ob42 that change positions or orientations in the virtual space constructed within the stereoscopic image area A4 is displayed.

At the bottom of the stereoscopic image area A4, the number count buttons G41 and G42 which is the user interface is displayed. The number count buttons G41 and G42 list the number of objects Ob41 or Ob42 that are expected to appear.

Objects related to the same item among multiple types of objects are simultaneously displayed while varying the depth in the virtual space. In the example shown, tomatoes (object Ob41) and apples (object Ob42) are displayed as multiple types of objects, the same item is displayed as identical items for both tomatoes and apples respectively, the items are of the same size (volume occupied in the virtual space) in the virtual space, and size appears to change due to varying depth.

Displayed number of objects related to the same item, such as number of displayed tomatoes in case of tomatoes or number of displayed apples in case of apples, and the accuracy of the user operation with respect to the number count buttons G41 and G42 are recorded as the as the test results of tachistoscopic vision and size constancy test.

Also, memory skills test is implemented after constancy measurement with a time difference by asking questions on the number of objects displayed related to the same item and receiving the answer from the observer. Questions on the number of objects related to the same item, such as number of tomatoes in case of tomatoes or number of apples in case of apples and accuracy of the answer given by the user are recorded as results of the memory skills test.

The above-described check and training program operates as follows.

First, when the program is started, operating conditions are set and the object for executing the operation according to the set conditions is generated in step S401.

The operation settings for the present embodiment is as follows.

Spatial cognitive ability test is carried out by setting depth to the general tachistoscopic vision, and memory skills test is carried out based on the answers given to different questions.

Constancy test to ascertain the size will be performed.
The number of displays are set from 1 to 10 such that the level of difficulty increases with the increase in the number.
The number of items to be displayed are set from 1 to 5 such that the level of difficulty increases with the increase in the number.
The number of colors are set from 1 to 5 such that the level of difficulty increases with the increase in the number.
Depth setting is set to depth, center, front, and standard 3 to 5 levels and can be input as a number.
Display range is 5 levels from the center.
Number of questions is set to 1 to 10, and can be set to any number.
Degree of difficulty can be set to 5 levels, "Very easy", "Easy", "Normal", "Difficult" and "Very difficult".
Display level can be set to 5 levels, "Very easy", "Easy", "Normal", "Difficult" and "Very difficult".
Evaluation criteria are the number of correct answers, judgment time, time required to answer the questions.
As the memory skills of the final question will be evaluated after another test from number of items remembered, number of displayed items, and number of correct answers.

The marks to be displayed can be selected from shapes, numbers, alphabets, Kanji, Hiragana, Katakana, animals, plants, fish, food, vegetables, fruits, and vehicles.

Next, operation of the objects starts in step S402. This operation starts automatically after operation conditions are set or with start instructions based on user operations. Step S403, loop process ("N" in S403) for user operation (or timeout). Measurement of elapsed time timing when the object has changed starts during this time. Elapsed time is reset when the object changes without user operation and information that the user has not responded is stored as the no-response history.

In step S403, when there is a user operation or after the predetermined time has elapsed ("Y" in S403), process exits the loop process and moves to step S404. In step S404, response time of user and accuracy of operations are recorded. If no-response history is available during the loop process in step S403, object operation at that time, no-response time and number of resets are recorded.

Completion of all object operations is determined in step S405, if there is a next operation ("N" in S405), the process proceeds to the next operation and steps S401 to S404 are repeated, and if all the operations have ended ("N" in S403), the process proceeds to step S406. In step S406, measurement results are tabulated, tachistoscopic vision and size constancy is diagnosed, and results are output.

After completion of tests such as tachistoscopic vision, memory skills test is performed (S407). Queries the number of objects displayed with tachistoscopic vision after a predetermined time has elapsed and determines the response time and accuracy. Step S408, loop process ("N" in S408) for user operation (or timeout). Measurement of elapsed time from the question starts during this time. Elapsed time is reset if the next question is asked without user operation and information that the user has not responded is stored as the no-response history.

In step S408, when there is a user operation or after the predetermined time has elapsed ("Y" in S408), process exits the loop process and moves to step S409. In step S409, response time of user and accuracy of operations are recorded. If no-response history is available during the loop process in step S408, object operation at that time, no response time and number of resets are recorded. In step S410, measurement results are tabulated, memory skills are diagnosed, and results are output.

According to the present program, for example, a plurality of fruits types such as apples and oranges are displayed at the same time while changing the depth, and the observer is made to answer the displayed number. Tachistoscopic vision and size constancy of the user can be checked by changing only the depth (depth in the virtual space) during display after setting identical items to the same size in the virtual space. If the time taken to answer or number of incorrect answers exceeds (falls below) a predetermined threshold value, there is a possibility of cognitive impairment, and preventive measures can be taken based on this. In the present embodiment, in addition to the tests with the stereoscopic viewing program, states of tension, relaxation, and concentration of an observer can be measured by analyzing the strength and balance of various electroencephalograms to understand their correlation with the accuracy of user operations, and this enables accuracy of early detection and prevention of mild dementia to be improved.

In addition to the tachistoscopic vision and size constancy, if the number of incorrect answers exceeds (falls below) a predetermined threshold value for questions related to memory skills, there is a possibility of cognitive impairment, and preventive measures can be taken based on this.

(5) Check and Training Program 5

Figure 11A:
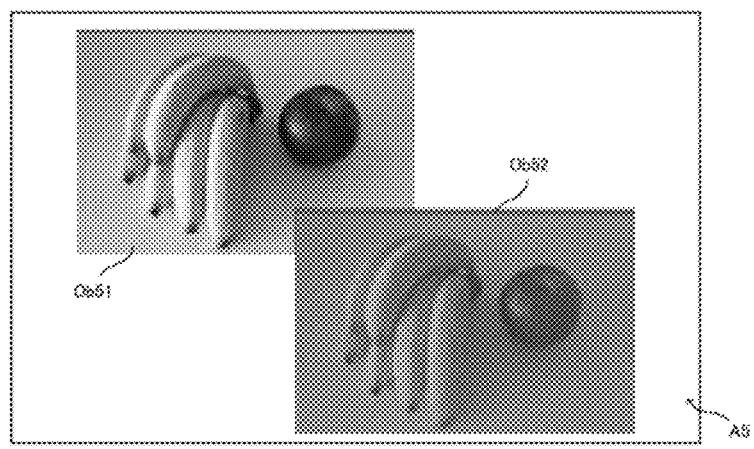
FIG. 11A-FIG. 11D is an explanatory diagram showing the screen configuration of the check and training program 5 according to the embodiment.
Figure 11B:
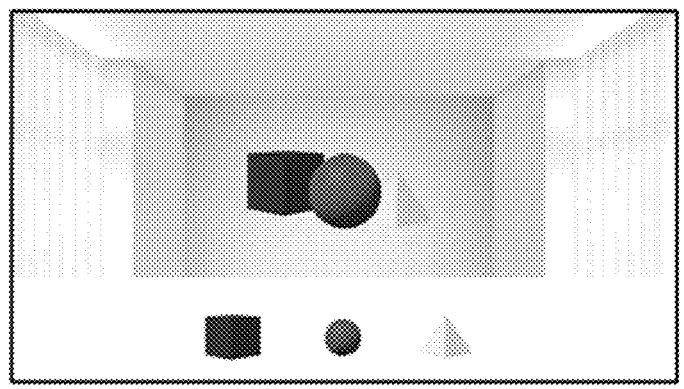
Figure 11C:
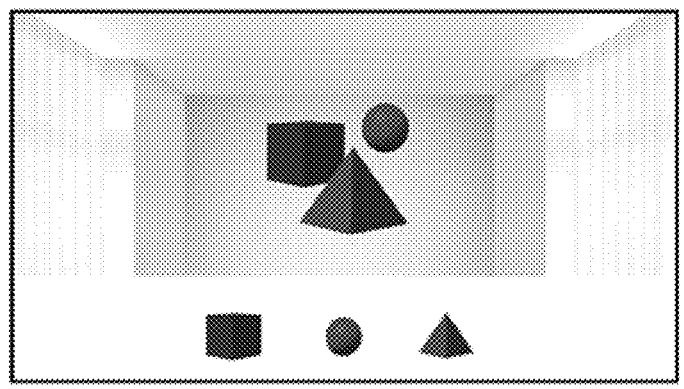
Figure 11D:
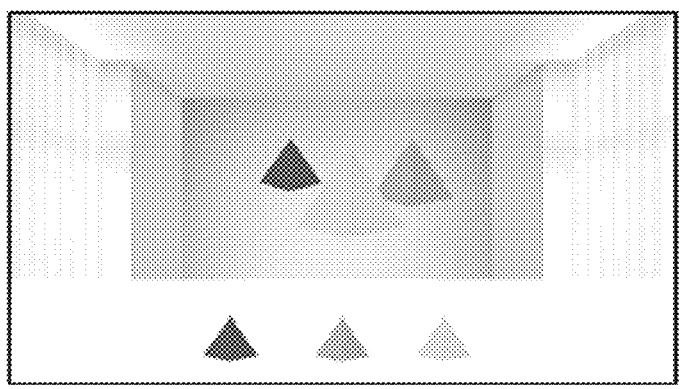
Figure 12:
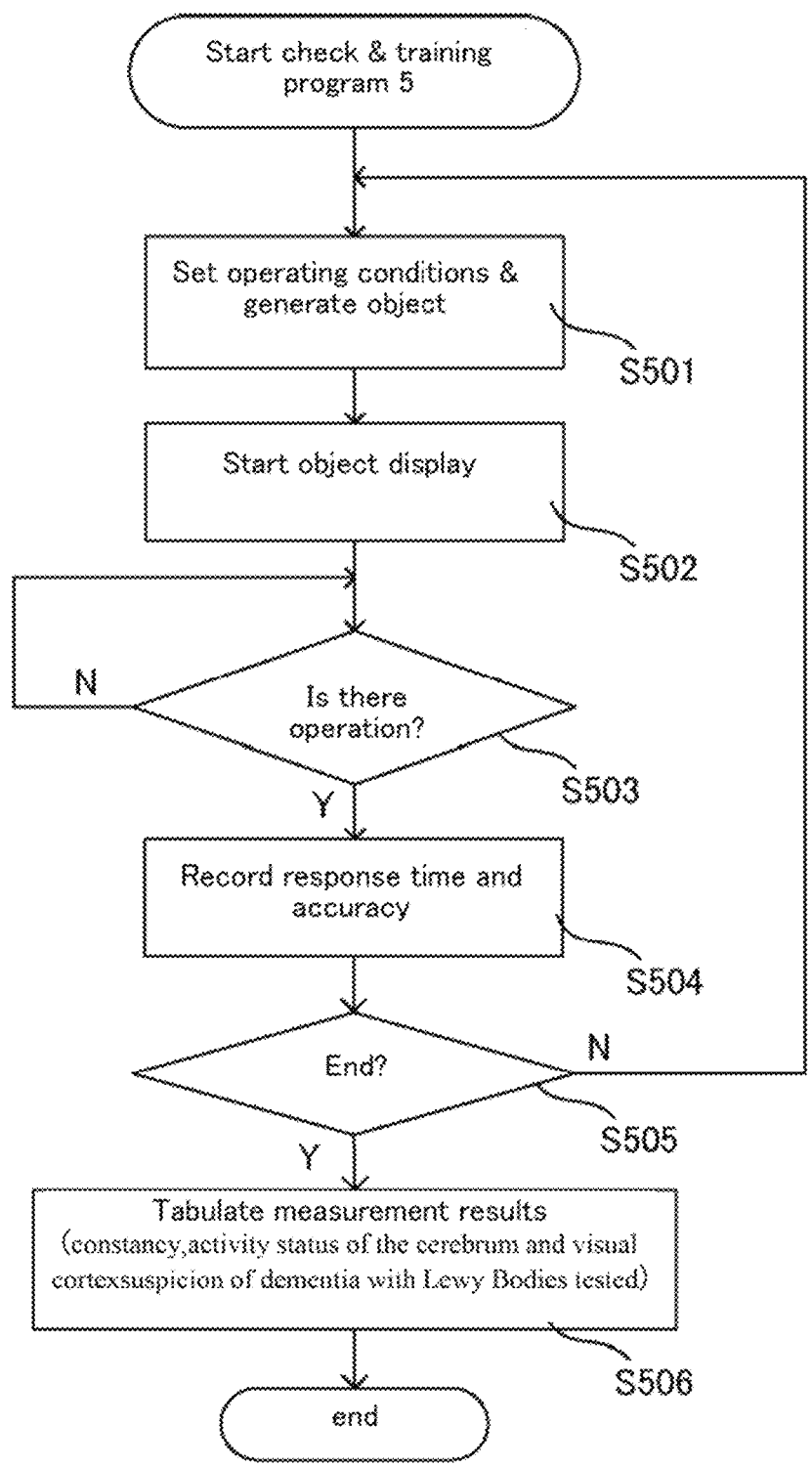
FIG. 12 is a flowchart showing the operations of the check and training program 5 according to the embodiment.

FIG. 11A-FIG. 11D is an explanatory diagram showing the screen configuration of the check and training program 5 and FIG. 12 is a flowchart showing the operations of the program. In the check and training program 5, light and dark, blue, green, red, yellow, cyan, magenta, and position of light source is adjusted with color filters to check if color constancy is functioning normally, and activity status of the cerebrum and visual cortex is measured to check for any suspicion of dementia with Lewy Bodies.

In the present program, as shown in FIG. 11A, a stereoscopic image area A5 is generated in which a stereoscopic image constituted by generating a convergence angle and parallax between the left eye image and right eye image is displayed and multiple objects Ob51, Ob52 that change positions or orientations in the virtual space constructed within the stereoscopic image area A5 is displayed. Objects Ob51, Ob52 related to the same item among multiple types of objects are displayed while varying brightness, saturation, color or position of light source.

In the stereoscopic image area, objects Ob51, Ob52 are selected with a user interface such as a touch screen. The number of displayed objects related to the same item and accuracy of screen touch are recorded as test results of the color constancy test.

The above-described check and training program operates as follows.

First, when the program is started, operating conditions are set and the object for executing the operation according to the set conditions is generated in step S501.

The operation settings for the present embodiment,

The object continues to be displayed up to the time an answer is provided. However, the time required for the user to answer after the object is displayed is recorded as response time. When the answer changes from the previous answer, elapsed time and correct/incorrect answer is recorded. Activity status of visual cortex V4 of the cerebrum is checked based on whether the color of the displayed object is recognized or not.

The photos and images to be displayed can be selected from shapes, numbers, alphabets, Kanji, Hiragana, Katakana, animals, plants, fish, food, vegetables, fruits, and vehicles can be selected.

Next, operation of the objects starts in step S502. This operation starts automatically after operation conditions are set or with start instructions based on user operations. Step S503 is a loop process ("N" in S503) for user operation. Measurement of elapsed time from when the object has changed starts during this time. Elapsed time is reset when the object changes without user operation and information that the user has not responded is stored as the no-response history.

In step S503, when there is a user operation ("Y" in S503), process exits the loop process and moves to step S504. In step S504, response time of user and accuracy of operations are recorded. If no-response history is available during the loop process in step S503, object operation at that time, no response time and number of resets are recorded.

Completion of all object operations is determined in step S505, if there is a next operation ("N" in S505), the process proceeds to the next operation and steps S501 to S504 are repeated, and if all the operations have ended ("N" in S503), the process proceeds to step S506. In step S506, measurement results are tabulated, color constancy is diagnosed, and results are output.

According to the present program, objects related to the same item are displayed by changing the brightness, saturation, color or light source position, and the observer is made to answer the color of the same item. By comparing the object color with the answer of the observer, color constancy of the observer can be checked. If the time taken to answer or number of incorrect answers exceeds (falls below) a predetermined threshold value, there is a possibility of cognitive impairment, and preventive measures can be taken based on this.

In the above example, a similar image with the arrangement of the fruit shown in FIG. 11A has been used as the object, for the other image, a color filter has been used to adjust bright and dark, blue, green, red, yellow, cyan, magenta and position of light source, but for example, as shown in FIG. 11B-FIG. 11D, an image in which the context of objects with different colors and shapes can also be used. Color, size, and arrangement of the objects can be changed for the image based on the level of difficulty, objects of different colors such as red, blue, and yellow shown in FIG. 11B are used as objects with low difficulty, and as the difficulty increases, similar colors are used as shown in FIG. 11C and FIG. 11D.

In the brain, because distance, shape and length and longitudinal context are processed from visual information of both eyes with depth perception, the above program can be used to train color and spatial perception. By making the users identify similar colors at high level of difficulty, training can be provided for perceptual information processing ability that is used to recognize color constancy from change in colors accompanying depth.

(6) Visual Training Program

Figure 13:
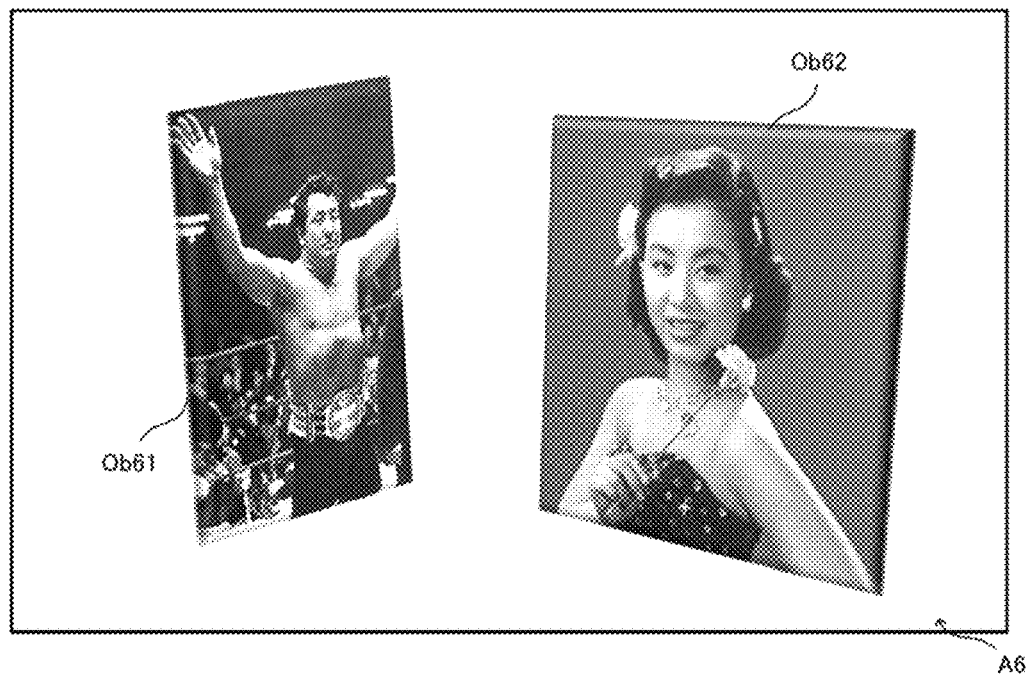
FIG. 13 is an explanatory diagram showing the screen configuration of the visual training program according to the embodiment.
Figure 14:
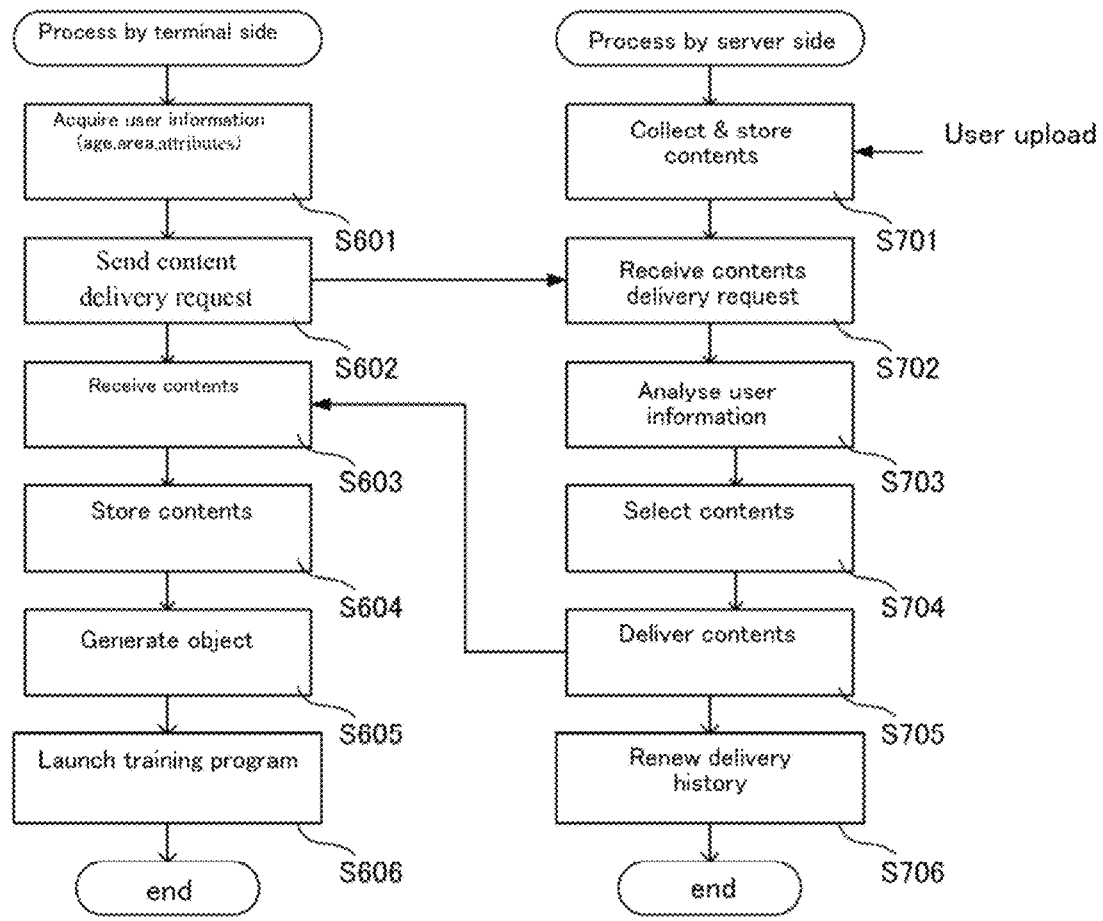
FIG. 14 is a flowchart showing the operations of the visual training program according to the embodiment.

FIG. 13 is an explanatory diagram showing the screen configuration of the check and training program 5 and FIG. 14 is a flowchart showing the operations of the program. The visual training program is a special program to prevent presbyopia and activate the brain by just viewing.

In the present embodiment, images uploaded to the content management server 3 is stored in association with the information including age of the subject shown in the image, and data is sent and received to/from the program being executed in the information processing terminal 1. Content management server 3 retrieves the delivery request that includes the age of the observer being tested from information processing terminal 1 and selects the image matching with the age of observer included in the delivery request from content database 34 and delivers to the program being executed in the information processing terminal 1.

The above check and training program operates as follows.

As shown in FIG. 14, in the present embodiment, content management server 3 associates the information including age of the subject shown in the image with the image that is uploaded by the user and stores (S701).

In the information processing terminal 1, attributes such as age, area where the person was born and raised, male, female, academic background and work history of the user who is the observer is acquired (S601), included in the content delivery request, and sent to the content management server 3 (S602).

The content management server 3 that has received this content delivery request (S702) analyzes the delivery request that includes the age of the observer being tested and selects (S704) the image matching with the age of observer included in the delivery request from content database 34 and delivers (S705) to the program being executed in the information processing terminal 1.

Information processing terminal 1 stores the contents received (S603, S604), creates objects using the contents (S605), and enables the objects to be used by the visual training program and various other training programs.

According to the present program, many users are asked to upload nostalgic photographs along with information containing age, which are accumulated in the form of a database, and images matched with the age of a user who is the subject with cognitive impairment are generated as object and used in various tests based on the above-mentioned program. As a result, long-term memory of the subject can be evoked during the various tests described above, and activation of the brain can be promoted.

(Program Recording Media)

The program of the above-described embodiment, as shown in FIG. 19, can be installed in a smartphone 171 integrated with mobile phone and communication functions, personal computer 172 used by the client, server device 173 or tablet PC 174 or IC chip 186 that is arranged on the network and provides data and functions to the client and executed on the CPU to easily construct a system having the above-mentioned functions. These programs, for example, can be distributed through communication lines or transferred as a package application operating on a stand-alone computer.

Such type of programs can be recorded on recording media 181 to 185 that can be read on personal computer. Specifically, program can be recorded in various recording media such as magnetic recording media such as flexible disk 183 or cassette tape 182, optical disk 181 such as CD-ROM or DVD-ROM, as well as media such as USB memory 185 or memory card 184.

(Stereoscopic Image Observation Device)

Figure 17A:
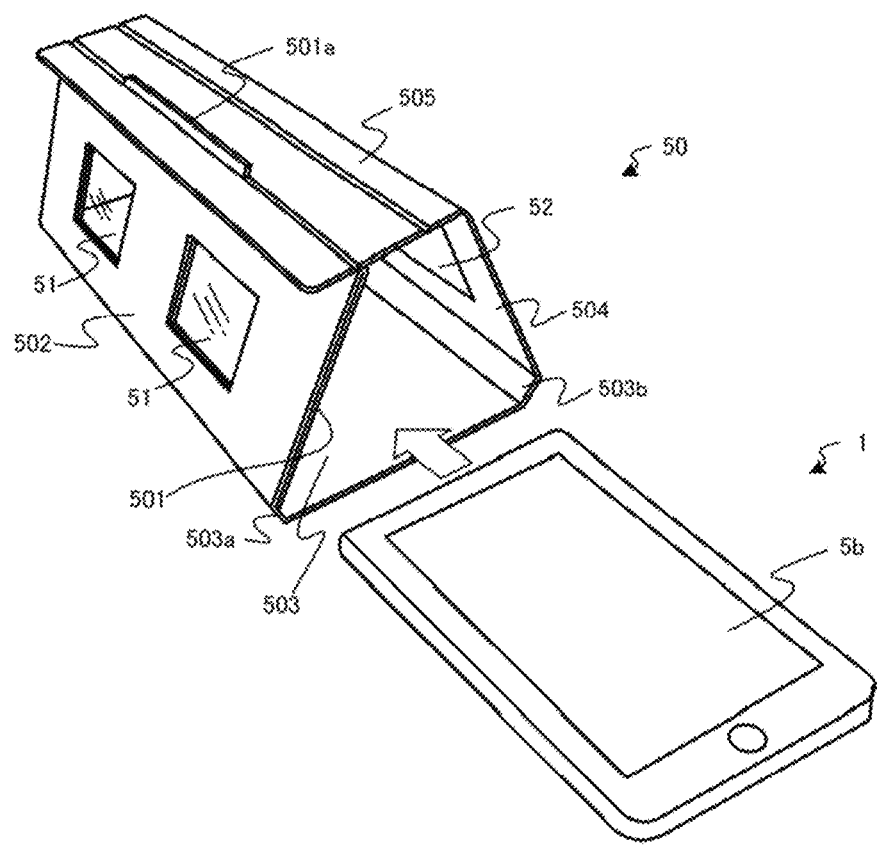
FIG. 17A is a perspective view showing the overall configuration of the stereoscopic image observation device according to the embodiment.
Figure 17B:
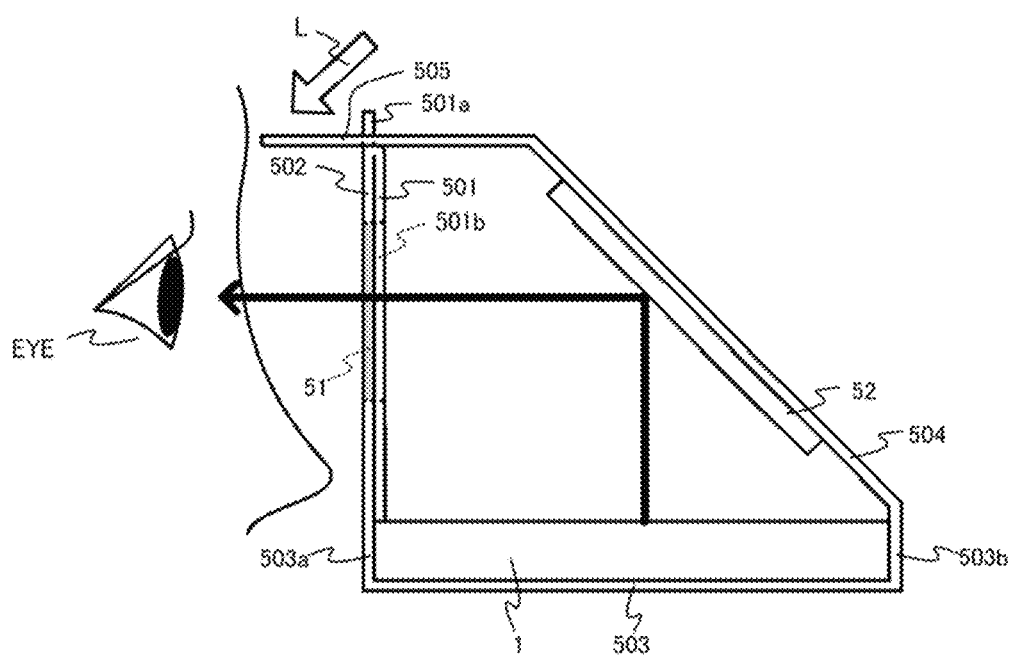
FIG. 17B is an explanatory diagram from the side view for the information processing terminal 1 arranged in a housing according to the embodiment.
Figure 18A:
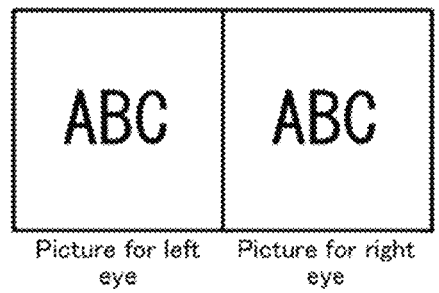
FIG. 18A, FIG. 18B is an explanatory diagram showing the left and right images displayed on the information processing terminal according to the embodiment.
Figure 18B:
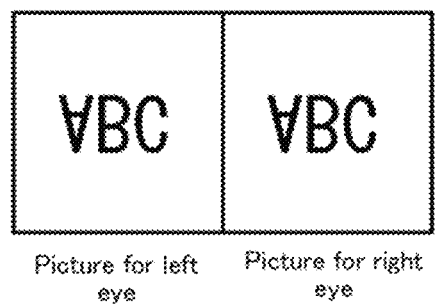

In the embodiment described above, the information processing terminal 1 that has been used enables stereoscopic viewing with the naked eye, but a stereoscopic image observation device can be combined with a general information processing terminal so that stereoscopic images can be viewed. FIG. 17A is a perspective view showing the overall configuration of the stereoscopic image observation device, FIG. 17B is an explanatory diagram from the side view for the information processing terminal 1 arranged in a housing. FIG. 18A, FIG. 18B is an explanatory diagram showing the left and right images displayed on the information processing terminal.

As shown in FIG. 17A, FIG. 17B, the image observation device is used to view the images (FIG. 18B) displayed on touch panel 5*b* of the information processing terminal 1 and is configured from a information processing terminal 1 and housing 50 that houses the information processing terminal 1.

Housing 50 is formed from paper or plastic and has an inner hollow space that is roughly rectangular in shape. Housing 50 is equipped with lens unit 502 that forms the surface placed in front of observer, base unit 503 that forms the bottom of housing 50 and on which the information processing terminal 1 is installed, and mirror unit 504 equipped with mirror 52 supported between lens 502 and base unit 503 that reflects light of the image displayed on information processing terminal 1 to lens unit 502. A light shield unit 505 that projects in the outward direction perpendicular to the surface of lens unit 502 is also provided in the upper part of lens unit 502.

Lens unit 502 is connected to one end of base unit 503 and mirror unit 504 is connected to the other end. Light shield unit 505 is connected to the end that is on the opposite side of the end at which base unit 503 is connected to mirror unit 504. Reinforcement 501 is connected to the end that is on the opposite side of the end at which base unit 503 is connected to lens unit 502. Folding or perforated lines is formed in the connecting part of each unit so that the respective sections can be bent inwards.

In lens unit 502, locations corresponding to left and right eye are cut and pair of lens 51, 51 is formed respectively in the corresponding portions. Pair of lens 21, 21 is an ocular lens that magnifies the real image created at the focal point and arranged on the lens unit 202 at locations corresponding to left and right eyes. There is no restriction on the shape of lens, for example, sheet shaped Fresnel lens that has sawtooth shape cross sections can also be used by dividing normal convex lens into concentric shape and reducing the thickness.

Mirror 52 is affixed on mirror unit 504 so that the light of the images for right and left eyes that is displayed on information processing terminal 1 is reflected to the respective lens 51, 51. During assembly, mirror 52 is formed on the surface facing the opposite side of base unit 503.

A standard display is provided in base unit 203 for matching with the image position displayed on display unit 50*a*. If the base unit 503 is bent along the respective folding lines formed in the vicinity of both ends of base unit 503, right side unit 503*b* and left side unit 503*a* that are in contact with the sides of the information processing terminal 1 is formed.

In base unit 503, holder 53 may be provided to hold the information processing terminal 1 at an appropriate position on base unit 503. Holder 53 is a member used to decide the position of information processing terminal 1, for example, a member formed from flexible members such as sponge or urethane is arranged on base unit 503 and the information processing terminal 1 is supported by bringing in contact with the sides surface of information processing terminal 1. As holder 53, for example, a U-shaped cut is formed on a part of base unit 503, the part surrounded by the cut is bent to the side where information processing terminal 1 is installed and is made to hold by bringing in contact with the sides of information processing terminal 1.

In the present embodiment, lens unit 502 and reinforcement 501 can be folded along the folding lines connecting them, during usage, lens unit 502 and reinforcement 501 overlap each other as shown in FIG. 16A, FIG. 16B. Through holes 501*b*, 501*b* with the shape same as of the pair of lens 51, 51, are provided in reinforcement 501. Even if reinforcement 501 and lens unit 502 overlap each other, reinforcement section 501 does not block the light of the image reflected from the mirror 52.

In addition, in the present embodiment, a U-shaped cut is formed in the folding line part where lens unit 502 and reinforcement 501 are connected, and by bending the folding lines the convex unit 501*a* that protrudes in the outward direction is formed. Light shield unit 505 is provided with an engagement hole 505*a* that passes through the light shield unit 505. Convex unit 501*a* is passed through the engagement hole 505*a* while assembling housing 50 to maintain the three-dimensional shape of the housing 50.

Light shield unit 505 is a member that blocks light from the outside, in the present embodiment, mirror unit 504 blocks the external light flowing inside the housing more than engagement hole 505*a*, and portion on the observer side blocks the external light shining on the eyes of the observer more than engagement hole 505*a*. One end 505*b* that is on the opposite side of the end at which mirror unit 504 is connected to the light shield unit 505 has a curved shape formed towards the engagement hole 505*a*.

In such type of an image observation device, when housing 50 is assembled, as shown in FIG. 17A, FIG. 17B, lens unit 502 will be raised in the perpendicular direction to the surface of display unit 50a of information processing terminal 1, and mirror unit 504 is inclined at approximately 45 degrees angle to the surface of display unit 50a.

When information processing terminal 1 is housed inside and the stereoscopic image (FIG. 18B) is displayed on display unit 50a, light of the image that is emitted from display unit 50a will be made to fall on mirror unit 504. When light of the image enters mirror unit 504, the light is reflected by mirror 52 and is emitted towards the pair of lens 51, 51. As shown in FIG. 18A, image for right eye and image for left eye enters respectively in the pair of lens 51, 51, and stereoscopic image can be viewed in with the EYE of the observer.

Note that, this invention is not limited to the above-mentioned embodiments. Although it is to those skilled in the art, the following are disclosed as the one embodiment of this invention.

Mutually substitutable members, configurations, etc. disclosed in the embodiment can be used with their combination altered appropriately.

Although not disclosed in the embodiment, members, configurations, etc. that belong to the known technology and can be substituted with the members, the configurations, etc. disclosed in the embodiment can be appropriately substituted or are used by altering their combination.

Although not disclosed in the embodiment, members, configurations, etc. that those skilled in the art can consider as substitutions of the members, the configurations, etc. disclosed in the embodiment are substituted with the above mentioned appropriately or are used by altering its combination.

While the invention has been particularly shown and described with respect to preferred embodiments thereof, it should be understood by those skilled in the art that the foregoing and other changes in form and detail may be made therein without departing from the sprit and scope of the invention as defined in the appended claims.

DESCRIPTION OF THE REFERENCE NUMERALS

A1~5 Stereoscopic image area
A3 Left and right image area
A31 Left eye image
A32 Right eye image
EYE Eye
G1 Judgment button
G21 Slider
G22, G23 Judgment button
G41, G42 Number count button
P11 Center point
P12, P13 Reciprocating point
P2 Center of gravity location
1 Information processing terminal
2 Communication Network
3 Contents distribution server
5a Speaker
5b Touch panel
6a Mouse
6b Keyboard
6c Microphone
6d Camera
10 CPU bus
11 CPU
12 Memory
13 Communication interface
14 Storage device
15 Output interface
16 Input interface
17 Model information acquisition unit
20 Parallax barrier
30 Lower layer
31 Communication unit
32 Authentication unit
33 User database
34 Contents database
35 Contents distribution unit
36 Control unit
37 Content management unit
40a LCD layer
40b Control unit
50 Housing
51, 51 Lens
52 Mirror member
53 Holder
60 Polarizer
61 EEG detection device
111 Application execution unit
112 Model information acquisition unit
113 Speech recognition unit
171 Smartphone
172 Personal computer
173 Server device
174 PC
181 to 185 Recording media
501 Reinforcement section
501a Convex unit
501b, 501b Through hole
502 Lens unit
503 Base unit
503a Left side unit
503b Right side unit
504 Mirror member
505 Light shielding unit

What is claimed is:

1. A system which includes a central processing unit (CPU), a memory, a communication interface, a storage device, an output interface and an input interface for detecting and preventing mild dementia comprising:

the CPU provided to execute a stereoscopic vision program configured to generate left eye image and right eye image corresponding to left and right eyes of an observer respectively;

a display unit provided to display the left eye image and the right eye image generated by the stereoscopic vision program executed by the CPU such that the left image can be viewed by the left eye only and the right image can be viewed by the right eye only; and a user interface configured to accept user inputs; wherein the CPU executes in the stereoscopic vision program, a stereoscopic image generating step, wherein a stereoscopic image is generated by generating a convergence angle and parallax between the left eye image and the right eye image;

an object depth variation step, wherein
the stereoscopic vision program generates multiple types of objects in the stereoscopic image,
the stereoscopic vision program changes positions or orientations of the multiple types of objects in the stereoscopic image, the stereoscopic vision program at least generates the multiple objects of same type among other multiple types of objects simultaneously to be displayed, the stereoscopic vision program varies a depth of the multiple objects of same type in the stereoscopic image;

and a constancy measurement step, wherein a displayed number of the multiple objects of the same type and accuracy of user inputs on the user interface are compared and determines that there is a possibility of cognitive impairment when the accuracy is below a predetermined threshold value.

2. The system for detecting and preventing mild dementia according to claim 1 wherein the CPU executes in the stereoscopic vision program, a query step, wherein memory skills test is implemented after constancy measurement step with a time difference by asking questions on the number of objects displayed of the same type and receiving an answer from the observer, and a memory skills measurement step, wherein the number of objects of the same type that are displayed and accuracy of the user inputs on the user interface are recorded as test results of the memory skills test.

* * * * *